United States Patent
Duncia et al.

(10) Patent No.: US 10,202,390 B2
(45) Date of Patent: Feb. 12, 2019

(54) HETEROARYL SUBSTITUTED AMINOPYRIDINE COMPOUNDS

(71) Applicant: BRISTOL-MYERS SQUIBB COMPANY, Princeton, NJ (US)

(72) Inventors: John V. Duncia, Newtown, PA (US); Daniel S. Gardner, Furlong, PA (US); John Hynes, Washington Crossing, PA (US); John E. Macor, Washington Crossing, PA (US); Satheesh Kesavan Nair, Bangalore (IN); Venkatram Reddy Paidi, Bangalore (IN); Joseph B. Santella, Springfield, PA (US); Kandhasamy Sarkunam, Hosur (IN); Ramesh Kumar Sistla, Bangalore (IN); Subba Rao Polimera, Karnataka (IN); Hong Wu, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/738,435

(22) PCT Filed: Jun. 23, 2016

(86) PCT No.: PCT/US2016/038862
§ 371 (c)(1),
(2) Date: Dec. 20, 2017

(87) PCT Pub. No.: WO2016/210037
PCT Pub. Date: Dec. 29, 2016

(65) Prior Publication Data
US 2018/0179213 A1 Jun. 28, 2018

(30) Foreign Application Priority Data
Jun. 24, 2015 (IN) .................................. 1880/DEL/15

(51) Int. Cl.
*C07D 487/04* (2006.01)

(52) U.S. Cl.
CPC .................................. *C07D 487/04* (2013.01)

(58) Field of Classification Search
None
See application file for complete search history.

(56) References Cited

U.S. PATENT DOCUMENTS

| | | |
|---|---|---|
| 8,575,153 B2 | 11/2013 | Kitamura et al. |
| 8,586,751 B2 | 11/2013 | De Lucca et al. |
| 9,663,467 B2 | 5/2017 | Moslin et al. |
| 2005/0272753 A1 | 12/2005 | Nagashima et al. |
| 2006/0148800 A1 | 7/2006 | Stadtmueller et al. |
| 2009/0082329 A1 | 3/2009 | Halley et al. |
| 2011/0230467 A1 | 9/2011 | Shirakami et al. |

FOREIGN PATENT DOCUMENTS

| | | |
|---|---|---|
| EP | 2 532 656 A1 | 12/2012 |
| GB | 2 388 596 A | 11/2003 |
| WO | WO 02/102800 A1 | 12/2002 |
| WO | WO 03/013523 A1 | 2/2003 |
| WO | WO 2004/065378 A1 | 8/2004 |
| WO | WO 2005/007646 A1 | 1/2005 |
| WO | WO 2005/075468 A2 | 8/2005 |
| WO | WO 2008/148889 A1 | 12/2008 |
| WO | WO 2009/046416 A1 | 4/2009 |
| WO | WO 2011/053701 A1 | 5/2011 |
| WO | WO 2012/149567 A1 | 11/2012 |
| WO | WO 2013/106612 A1 | 7/2013 |
| WO | WO 2013/106614 A1 | 7/2013 |
| WO | WO 2013/106641 A1 | 7/2013 |

(Continued)

OTHER PUBLICATIONS

Cushing, Leah. JBC Papers in Press (2017) Manuscript M117.796912.*
Seganish, W. Michael. Expert Opinion on Therapeutic Patents (2016) 26(8) 917-932.*
Auto-immune Diseases: MedlinePlus. (2014). Web: <https://www.nlm.nih.gov/medlineplus/autoimmunediseases.html>.*
Asthma. MayoClinic. (2018) Web: < https://www.mayoclinic.org/diseases-conditions/asthrna/symptoms-causes/syc-20369653>.*
Buckley, George M., "IRAK-4 inhibitors. Part 1: A series of amides", ScienceDirect, Bioorganic & Medicinal Chemistry Letters, 2008, vol. 18, pp. 3211-3214.

(Continued)

*Primary Examiner* — Deepak R Rao
*Assistant Examiner* — Laura M Daniel
(74) *Attorney, Agent, or Firm* — Gary Greenblatt

(57) ABSTRACT

Disclosed are compounds of Formula (I) or salts thereof, wherein: HET is a heteroaryl selected from imidazo[1,2-b]pyridazinyl and pyrazolo[1,5-a]pyrimidinyl, wherein said heteroaryl is attached to the pyridinyl group in the compound of Formula (I) by a carbon ring atom in the heteroaryl and wherein said heteroaryl is substituted with zero to 2 Rb; A is pyrazolyl, imidazolyl, or triazolyl, each substituted with zero or 1 Ra; and R3, Ra, and Rb are define herein. Also disclosed are methods of using such compounds as modulators of IRAK4, and pharmaceutical compositions comprising such compounds. These compounds are useful in treating, preventing, or slowing inflammatory and autoimmune diseases, or in the treatment of cancer.

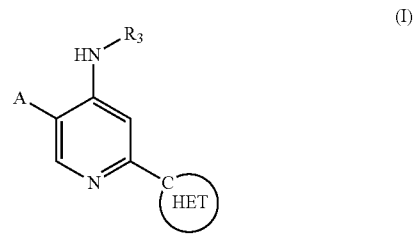

(I)

12 Claims, No Drawings

(56) References Cited

FOREIGN PATENT DOCUMENTS

| WO | WO 2014/074657 A1 | 5/2014 |
| WO | WO 2014/074660 A1 | 5/2014 |
| WO | WO 2014/074675 A1 | 5/2014 |
| WO | WO 2015/103453 A1 | 7/2015 |
| WO | WO 2016/210034 A1 | 12/2016 |
| WO | WO 2016/210037 A1 | 12/2016 |

OTHER PUBLICATIONS

Buckley, George M., et al., "IRAK-4 inhibitors. Part II: A structure-based assessment of imidazo[1,2-α]pyridine binding", ScienceDirect, Bioorganic & Medicinal Chemistry Letters, 2008, vol. 18, pp. 3291-3295.

Buckley, George M., et al., "IRAK-4 inhibitors. Part III: A series of imidazo[1,2-α]pyridines", ScienceDirect, Biorganic & Medicinal Chemistry Letters, 2008, vol. 18, pp. 3656-3660.

Hynes, John, et al., Annual Reports in Medicinal Chemistry, 2014, vol. 49, pp. 117-133.

Seganish, W. Michael, "Inhibitors of interleukin-1 receptor-associated kinase 4 (IRAK4): a patent review (2012-2015)", Expert Opinion on Therapeutic Patents, 2016, vol. 26, No. 8, pp. 917-932.

International Preliminary Report on Patentability, International application No. PCT/US2016/038862, dated Dec. 26, 2017.

\* cited by examiner

HETEROARYL SUBSTITUTED AMINOPYRIDINE COMPOUNDS

CROSS-REFERENCE TO RELATED APPLICATIONS

This application is a 371 application of International Application No. PCT/US2016/038862 filed on Jun. 23, 2016, which claims the benefit of Indian Provisional Patent Application Serial No. 1880/DEL/15, filed Jun. 24, 2015, the content of each is hereby fully incorporated by reference in its entirety for all purposes.

DESCRIPTION

The present invention generally relates to heteroaryl substituted aminopyridine compounds useful as kinase inhibitors, including the modulation of IRAK-4. Provided herein are heteroaryl substituted aminopyridine compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including IRAK-4 in a mammal.

Toll/IL-1 receptor family members are important regulators of inflammation and host resistance. The Toll like receptor (TLR) family recognizes molecular patterns derived from infectious organisms including bacteria, fungi, parasites, and viruses (reviewed in Kawai, T. et al., *Nature Immunol.*, 11:373-384 (2010)). Ligand binding to the receptor induces dimerization and recruitment of adaptor molecules to a conserved cytoplasmic motif in the receptor termed the Toll/IL-1 receptor (TIR) domain. With the exception of TLR3, all TLRs recruit the adaptor molecule MyD88. The IL-1 receptor family also contains a cytoplasmic TIR motif and recruits MyD88 upon ligand binding (reviewed in Sims, J. E. et al., *Nature Rev. Immunol.*, 10:89-102 (2010)).

Members of the IRAK family of serine/threonine kinases are recruited to the receptor via interactions with MyD88. The family consists of four members. Several lines of evidence indicate that IRAK4 plays a critical and non-redundant role in initiating signaling via MyD88 dependent TLRs and IL-1R family members. Structural data confirms that IRAK4 directly interacts with MyD88 and subsequently recruits either IRAK1 or IRAK2 to the receptor complex to facilitate downstream signaling (Lin, S. et al., *Nature*, 465: 885-890 (2010)). IRAK4 directly phosphorylates IRAK1 to facilitate downstream signaling to the E3 ubiquitin ligase TRAF6, resulting in activation of the serine/threonine kinase TAK1 with subsequent activation of the NFκB pathway and MAPK cascade (Flannery, S. et al., *Biochem. Pharmacol.*, 80:1981-1991 (2010)). A subset of human patients was identified who lack IRAK4 expression (Picard, C. et al., *Science*, 299:2076-2079 (2003)). Cells from these patients fail to respond to all TLR agonists with the exception of TLR3 as well as to members of the IL-1 family including IL-1β and IL-18 (Ku, C. et al., *J. Exp. Med.*, 204:2407-2422 (2007)). Deletion of IRAK4 in mice results in a severe block in IL-1, IL-18 and all TLR dependent responses with the exception of TLR3 (Suzuki, N. et al., *Nature*, 416:750-754 (2002)). In contrast, deletion of either IRAK1 (Thomas, J. A. et al., *J. Immunol.*, 163:978-984 (1999); Swantek, J. L. et al., *J. Immunol.*, 164:4301-4306 (2000) or IRAK2 (Wan, Y. et al., *J. Biol. Chem.*, 284:10367-10375 (2009)) results in partial loss of signaling. Furthermore, IRAK4 is the only member of the IRAK family whose kinase activity has been shown to be required for initiation of signaling. Replacement of wild type IRAK4 in the mouse genome with a kinase inactive mutant (KDKI) impairs signaling via all MyD88 dependent receptors including IL-1, IL-18 and all TLRs with the exception of TLR3 (Koziczak-Holbro, M. et al., *J. Biol. Chem.*, 282:13552-13560 (2007); Kawagoe, T. et al., *J. Exp. Med.*, 204:1013-1024 (2007); and Fraczek, J. et al., *J. Biol. Chem.*, 283:31697-31705 (2008)).

As compared to wild type animals, IRAK4 KDKI mice show greatly reduced disease severity in mouse models of multiple sclerosis (Staschke, K. A. et al., *J. Immunol.*, 183:568-577 (2009)), rheumatoid arthritis (Koziczak-Holbro, M. et al., *Arthritis Rheum.*, 60:1661-1671 (2009)), atherosclerosis (Kim, T. W. et al., *J. Immunol.*, 186:2871-2880 (2011) and Rekhter, M. et al., *Biochem. Biophys. Res. Comm.*, 367:642-648 (2008)), and myocardial infarction (Maekawa, Y. et al., *Circulation*, 120:1401-1414 (2009)). As described, IRAK4 inhibitors will block all MyD88 dependent signaling. MyD88 dependent TLRs have been shown to contribute to the pathogenesis of multiple sclerosis, rheumatoid arthritis, cardiovascular disease, metabolic syndrome, sepsis, systemic lupus erythematosus, inflammatory bowel diseases including Crohn's disease and ulcerative colitis, autoimmune uveitis, asthma, allergy, type I diabetes, and allograft rejection (Keogh, B. et al., *Trends Pharmacol. Sci.*, 32:435-442 (2011); Mann, D. L., *Circ. Res.*, 108:1133-1145 (2011); Horton, C. G. et al., *Mediators Inflamm.*, Article ID 498980 (2010), doi:10.1155/2010/498980; Goldstein, D. R. et al., *J. Heart Lung Transplant.*, 24:1721-1729 (2005); and Cario, E., *Inflamm. Bowel Dis.*, 16:1583-1597 (2010)). Oncogenically active MyD88 mutations in diffuse large B cell lymphomas have been identified that are sensitive to IRAK4 inhibition (Ngo, V. N. et al., *Nature*, 470:115-121 (2011)). Whole genome sequencing also identified mutations in MyD88 associated with chronic lymphatic leukemia suggesting that IRAK4 inhibitors may also have utility in treating leukemia (Puente, X. S. et al., *Nature*, 475:101-105 (2011)).

In addition to blocking TLR signaling, IRAK4 inhibitors will also block signaling by members of the IL-1 family. Neutralization of IL-1 has been shown to be efficacious in multiple diseases including gout; gouty arthritis; type 2 diabetes; auto-inflammatory diseases including Cryopyrin-Associated Periodic Syndromes (CAPS), TNF Receptor Associated Periodic Syndrome (TRAPS), Familial Mediterranean Fever (FMF), adult onset stills; systemic onset juvenile idiopathic arthritis; stroke; Graft-versus-Host Disease (GVHD); smoldering multiple myeloma; recurrent pericarditis; osteoarthritis; emphysema (Dinarello, C. A., *Eur. J. Immunol.*, 41:1203-1217 (2011) and Couillin, I. et al., *J. Immunol.*, 183:8195-8202 (2009)). In a mouse model of Alzheimer's disease, blockade of IL-1 receptor improved cognitive defects, attenuated tau pathology and reduced oligomeric forms of amyloid-β (Kitazawa, M. et al., *J. Immunol.*, 187:6539-6549 (2011)). IL-1 has also been shown to be a critical link to adaptive immunity, driving differentiation of the TH17 effector T cell subset (Chung, Y. et al., *Immunity*, 30:576-587 (2009)). Therefore, IRAK4 inhibitors are predicted to have efficacy in TH17 associated diseases including multiple sclerosis, psoriasis, inflammatory bowel diseases, autoimmune uveitis, and rheumatoid arthritis (Wilke, C. M. et al., *Trends Immunol.*, 32:603-661 (2011)).

WO2013/106612, WO2013/106614, WO2013/106641, WO2014/074657, and WO2014/074675 disclose substituted pyridyl compounds useful as kinase inhibitors, including the modulation of IRAK4.

In view of the conditions that may benefit by treatment involving modulation of protein kinases, it is immediately apparent that new compounds capable of modulating protein kinases such as IRAK-4 and methods of using these compounds could provide substantial therapeutic benefits to a wide variety of patients.

The present invention relates to a new class of heteroaryl substituted aminopyridine compounds found to be effective inhibitors of protein kinases including IRAK-4. These compounds are provided to be useful as pharmaceuticals with desirable stability, bioavailability, therapeutic index, and toxicity values that are important to their drugability.

SUMMARY OF THE INVENTION

The present invention provides to compounds of Formula (I) that are useful as inhibitors of IRAK-4, and are useful for the treatment of proliferative diseases, allergic diseases, autoimmune diseases and inflammatory diseases, or stereoisomers, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of IRAK-4 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

One embodiment provides a method for treating inflammatory and autoimmune diseases wherein the treatment of inflammatory diseases is even more preferred. Particular, inflammatory and autoimmune diseases include, but are not limited to, Crohn's disease, ulcerative colitis, asthma, graft versus host disease, allograft rejection, chronic obstructive pulmonary disease, Graves' disease, rheumatoid arthritis, systemic lupus erythematosus, lupus nephritis, cutaneous lupus, psoriasis, cryopyrin-associated periodic syndromes (CAPS), TNF receptor associated periodic syndrome (TRAPS), familial Mediterranean fever (FMF), adult onset stills, systemic onset juvenile idiopathic arthritis, multiple sclerosis, neuropathic pain, gout, and gouty arthritis.

One embodiment provides a method for treating gout and gouty arthritis.

An alternate preferred embodiment is a method for treating metabolic diseases, including type 2 diabetes and atherosclerosis.

One embodiment provides a method for treating cancer comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of cancers.

The present invention also provides processes and intermediates for making the compounds of the present invention or stereoisomers, tautomers, pharmaceutically acceptable salts, solvates, or prodrugs thereof.

These and other features of the invention will be set forth in the expanded form as the disclosure continues.

DETAILED DESCRIPTION

The first aspect of the present invention provides at least one compound of Formula (I):

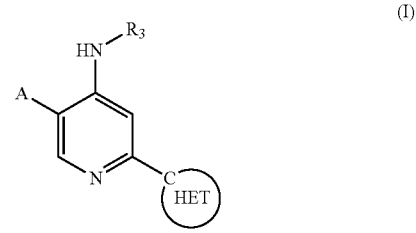

or a salt thereof, wherein:

HET is a heteroaryl selected from imidazo[1,2-b]pyridazinyl and pyrazolo[1,5-a]pyrimidinyl, wherein said heteroaryl is attached to the pyridinyl group in the compound of Formula (I) by a carbon ring atom in said heteroaryl and wherein said heteroaryl is substituted with zero to 2 $R_b$;

A is pyrazolyl, imidazolyl, or triazolyl, each substituted with zero or 1 $R_a$;

$R_3$ is:
  (i) —$CH_2CH_3$, —$CH(CH_3)_2$, —$CH_2CHF_2$, —$CH(CH_3)CH_2OH$, cyclopropyl, oxetanyl, or tetrahydropyranyl; or
  (ii) pyrazolyl substituted with zero to 2 substituents independently selected from $C_{1-3}$ alkyl, $C_{1-3}$ hydroxyalkyl, $C_{1-3}$ fluoroalkyl, oxetanyl, tetrahydrofuranyl, and tetrahydropyranyl;

$R_a$ is:
  (i) F, Cl, —OH, —CN, $C_{1-6}$ alkyl, $C_{1-4}$ fluoroalkyl, $C_{1-4}$ cyanoalkyl, or $C_{1-6}$ hydroxyalkyl; or
  (ii) $C_{3-6}$ cycloalkyl, azetidinyl, oxetanyl, tetrahydrofuranyl, tetrahydropyranyl, piperidinyl, piperazinyl, pyrrolyl, pyrrolidinonyl, morpholinyl, pyrrolidinyl, phenyl, pyrazolyl, imidazolyl, pyridinyl, or pyrimidinyl, each substituted with zero to 4 substituents independently selected F, —CN, —OH, —$NR_yR_y$, $C_{1-3}$ alkyl, $C_{1-3}$ fluoroalkyl, —CH(phenyl)$_2$, —O($C_{1-4}$ alkyl), —C(O)($C_{1-4}$ alkyl), —C(O)($C_{1-4}$ deuteroalkyl), —C(O)($C_{3-6}$ cycloalkyl), —C(O)O($C_{1-4}$ alkyl), —C(O)$NR_yR_y$, —C(O)(phenyl), —C(O)(pyridinyl), —C(O)$CH_2(C_{3-6}$ cycloalkyl), —NHC(O)$CH_3$, —NHC(O)$OCH_3$, —NHC(O)OC($CH_3$)$_3$, —S(O)$_2$($C_{1-3}$ alkyl), and —OS(O)$_2$($C_{1-3}$ alkyl);

each $R_b$ is independently selected from F, Cl, —CN, —$NH_2$, —$CH_3$, —$OCH_3$, and cyclopropyl;

and each $R_y$ is independently H or $C_{1-3}$ alkyl.

One embodiment provides a compound of Formula (I) or a salt thereof wherein HET is a heteroaryl selected from imidazo[1,2-b]pyridazinyl and pyrazolo[1,5-a]pyrimidinyl, wherein said heteroaryl is attached to the pyridinyl group in the compound of Formula (I) by a carbon ring atom in said heteroaryl and wherein said heteroaryl is substituted with zero to 1 $R_b$; A is pyrazolyl or triazolyl, each substituted with zero or 1 $R_a$; $R_3$ is —CH(CH$_3$)$_2$, cyclopropyl, or 2,2-difluoroethyl pyrazolyl; $R_a$ is —CH$_2$CH$_2$CH$_3$, —CH$_2$CF$_3$, —C(CH$_3$)$_2$OH, —CH$_2$C(CH$_3$)$_2$OH, —CH$_2$CH$_2$C(CH$_3$)$_2$OH, tetrahydropyranyl, acetylazetidinyl, or

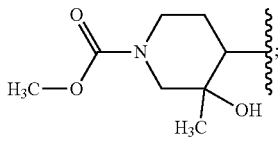

and $R_b$ is Cl or —CN.

One embodiment provides a compound of Formula (I) or a salt thereof wherein A is pyrazolyl substituted with zero or 1 $R_a$; and HET, $R_a$, and $R_3$ are defined in the first aspect. Included in this embodiment are compounds in which A is

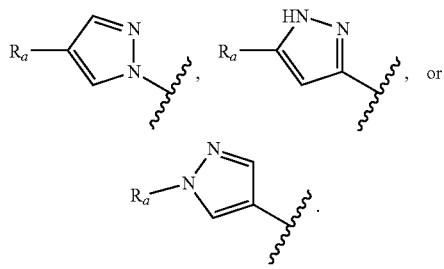

Also included in this embodiment are compounds in which $R_a$ is —CH$_2$CF$_3$, —CH$_2$CH$_2$CH$_3$, —C(CH$_3$)$_2$OH, —CH$_2$C(CH$_3$)$_2$OH, —CH$_2$CH$_2$C(CH$_3$)$_2$OH, or tetrahydropyran.

One embodiment provides a compound of Formula (I) or a salt thereof wherein A is pyrazolyl or imidazolyl substituted with zero or 1 $R_a$; and HET, $R_a$, and $R_3$ are defined in the first aspect. Included in this embodiment are compounds in which A is

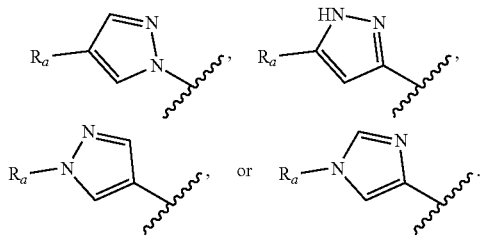

Also included in this embodiment are compounds in which $R_a$ is —CH$_2$CF$_3$, —CH$_2$CH$_2$CH$_3$, —C(CH$_3$)$_2$OH, —CH$_2$C(CH$_3$)$_2$OH, —CH$_2$CH$_2$C(CH$_3$)$_2$OH, or tetrahydropyran.

One embodiment provides a compound of Formula (I) or a salt thereof wherein A is imidazolyl substituted with zero or 1 $R_a$; and HET, $R_a$, and $R_3$ are defined in the first aspect. Included in this embodiment are compounds in which A is or

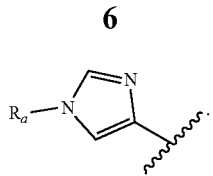

Also included in this embodiment are compounds in which $R_a$ is —CH$_2$CF$_3$, —CH$_2$CH$_2$CH$_3$, —C(CH$_3$)$_2$OH, —CH$_2$C(CH$_3$)$_2$OH, —CH$_2$CH$_2$C(CH$_3$)$_2$OH, or tetrahydropyran.

One embodiment provides a compound of Formula (I) or a salt thereof wherein A is triazolyl; and HET, $R_a$, and $R_3$ are defined in the first aspect. Included in this embodiment are compounds in which A is

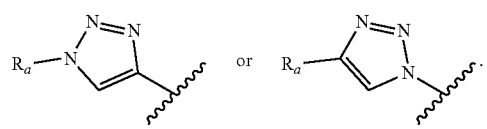

Also included in this embodiment are compounds in which $R_a$ is —CH$_2$CH$_2$CH$_3$, tetrahydropyranyl, acetylazetidinyl, or

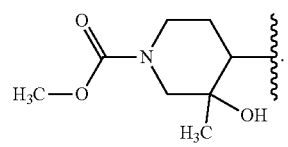 [SMILES: *C1CCN(C(=O)OC)CC1(C)O]

One embodiment provides a compound of Formula (I) or a salt thereof wherein A is pyrazolyl or triazolyl; and HET, $R_a$, and $R_3$ are defined in the first aspect. Included in this embodiment are compounds in which A is

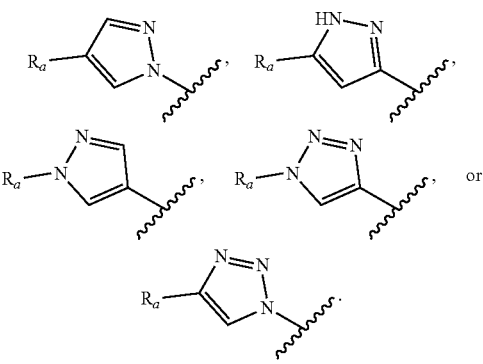

Also included in this embodiment are compounds in which $R_a$ is —CH$_2$CH$_2$CH$_3$, —CH$_2$CF$_3$, —C(CH$_3$)$_2$OH, —CH$_2$C(CH$_3$)$_2$OH, —CH$_2$CH$_2$C(CH$_3$)$_2$OH, tetrahydropyranyl, acetylazetidinyl, or

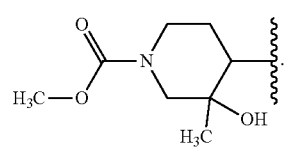 [SMILES: *C1CCN(C(=O)OC)CC1(C)O]

One embodiment provides a compound of Formula (I) or a salt thereof wherein HET is

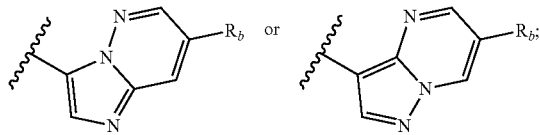

and A, $R_b$, and $R_3$ are defined in the first aspect. Included in this embodiment are compounds in which $R_b$ is Cl or —CN. Also included are compounds in which $R_3$ is —CH(CH$_3$)$_2$, cyclopropyl, or 2,2-difluoroethyl pyrazolyl.

One embodiment provides a compound of Formula (I) or a salt thereof wherein HET is imidazo[1,2-b]pyridazinyl, wherein said imidazo[1,2-b]pyridazinyl is attached to the pyridinyl group in the compound of Formula (I) by a carbon ring atom in said imidazo[1,2-b]pyridazinyl and wherein said imidazo[1,2-b]pyridazinyl is substituted with zero to 2 $R_b$; and A, $R_b$, and $R_3$ are defined in the first aspect. Included in this embodiment are compounds in which HET is

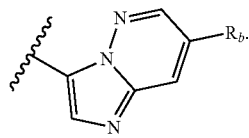

Also included are compounds in which $R_b$ is Cl or —CN.

One embodiment provides a compound of Formula (I) or a salt thereof wherein HET is pyrazolo[1,5-a]pyrimidinyl, wherein said pyrazolo[1,5-a]pyrimidinyl is attached to the pyridinyl group in the compound of Formula (I) by a carbon ring atom in said pyrazolo[1,5-a]pyrimidinyl and wherein said pyrazolo[1,5-a]pyrimidinyl is substituted with zero to 2 $R_b$; and A, $R_b$, and $R_3$ are defined in the first aspect. Included in this embodiment are compounds in which HET is

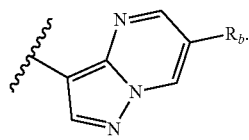

Also included are compounds in which $R_b$ is Cl or —CN.

One embodiment provides a compound of Formula (I) or a salt thereof wherein $R_3$ is —CH(CH$_3$)$_2$, cyclopropyl, or 2,2-difluoroethyl pyrazolyl; and HET and A are defined in the first aspect. Included in this embodiment are compounds in which $R_3$ is —CH(CH$_3$)$_2$ or cyclopropyl. Also included are compounds in which $R_3$ is —CH(CH$_3$)$_2$.

One embodiment provides a compound of Formula (I) or a salt thereof wherein $R_a$ is F, Cl, —OH, —CN, $C_{1-6}$ alkyl, $C_{1-4}$ fluoroalkyl, $C_{1-4}$ cyanoalkyl, or $C_{1-6}$ hydroxyalkyl; and HET, A, and $R_3$ are defined in the first aspect. Included in this embodiment are compounds in which $R_a$ is $C_{2-4}$ alkyl, $C_{2-4}$ fluoroalkyl, $C_{1-3}$ cyanoalkyl, or $C_{2-6}$ hydroxyalkyl. Also included in this embodiment are compounds in which $R_a$ is —CH$_2$CH$_2$CH$_3$, —CH$_2$CF$_3$, or —C(CH$_3$)$_2$OH, —CH$_2$C(CH$_3$)$_2$OH, or —CH$_2$CH$_2$C(CH$_3$)$_2$OH.

One embodiment provides a compound of Formula (I) or a salt thereof wherein $R_a$ is $C_{3-6}$ cycloalkyl, azetidinyl, oxetanyl, tetrahydrofuranyl, tetrahydropyranyl, piperidinyl, piperazinyl, pyrrolyl, pyrrolidinonyl, morpholinyl, pyrrolidinyl, phenyl, pyrazolyl, imidazolyl, pyridinyl, or pyrimidinyl, each substituted with zero to 4 substituents independently selected F, —CN, —OH, —NR$_y$R$_y$, $C_{1-3}$ alkyl, $C_{1-3}$ fluoroalkyl, —CH(phenyl)$_2$, —O(C$_{1-4}$ alkyl), —C(O)(C$_{1-4}$ alkyl), —C(O)(C$_{1-4}$ deuteroalkyl), —C(O)(C$_{3-6}$ cycloalkyl), —C(O)O(C$_{1-4}$ alkyl), —C(O)NR$_y$R$_y$, —C(O)(phenyl), —C(O)(pyridinyl), —C(O)CH$_2$(C$_{3-6}$ cycloalkyl), —NHC(O)CH$_3$, —NHC(O)OCH$_3$, —NHC(O)OC(CH$_3$)$_3$, —S(O)$_2$(C$_{1-3}$ alkyl), and —OS(O)$_2$(C$_{1-3}$ alkyl); and HET, A, and $R_3$ are defined in the first aspect. Included in this embodiment are compounds in which $R_a$ is azetidinyl, oxetanyl, tetrahydrofuranyl, tetrahydropyranyl, piperidinyl, or piperazinyl, each substituted with zero to 4 substituents independently selected F, —CN, —OH, —NR$_y$R$_y$, $C_{1-3}$ alkyl, $C_{1-2}$ fluoroalkyl, —O(C$_{1-2}$ alkyl), —C(O)(C$_{1-2}$ alkyl), —C(O)(C$_{1-2}$ deuteroalkyl), —C(O)(C$_{3-6}$ cycloalkyl), —C(O)O(C$_{1-4}$ alkyl), —C(O)NR$_y$R$_y$, —C(O)O(C$_{1-4}$ alkyl), —NHC(O)CH$_3$, —NHC(O)OCH$_3$, —S(O)$_2$(C$_{1-2}$ alkyl), and —OS(O)$_2$(C$_{1-2}$ alkyl). Also included in this embodiment are compounds in which $R_a$ is tetrahydropyranyl, acetylazetidinyl, or

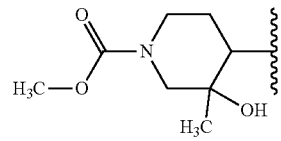

One embodiment provides a compound of Formula (I) or a salt thereof wherein each $R_b$ is independently selected from F, Cl, —CN, —NH$_2$, —CH$_3$, and cyclopropyl; and HET, A, and $R_3$ are defined in the first aspect. Included in this embodiment are compounds in which each $R_b$ is independently selected from F, Cl, —CN, —NH$_2$, and —CH$_3$. Also included are compounds in which each $R_b$ is independently selected from Cl and —CN.

One embodiment provides a compound of Formula (I) or a salt thereof, wherein said compound is selected from: 3-(5-(4-(2-hydroxypropan-2-yl)-1H-pyrazol-1-yl)-4-(isopropylamino)pyridin-2-yl) pyrazolo[1,5-a]pyrimidine-6-carbonitrile (1); 2-(7-chloroimidazo[1,2-b]pyridazin-3-yl)-N-isopropyl-5-(4-(tetrahydro-2H-pyran-4-yl)-1H-pyrazol-1-yl)pyridin-4-amine (2); 3-(4-(isopropylamino)-5-(1-(tetrahydro-2H-pyran-4-yl)-1H-pyrazol-4-yl)pyridin-2-yl)imidazo[1,2-b]pyridazine-7-carbonitrile (3); 1-(4-(6-(7-chloroimidazo[1,2-b]pyridazin-3-yl)-4-(isopropylamino)pyridin-3-yl)-1H-pyrazol-1-yl)-2-methylpropan-2-ol (4); 3-(5-(1-(2-hydroxy-2-methylpropyl)-1H-pyrazol-4-yl)-4-(isopropylamino)pyridin-2-yl)imidazo[1,2-b]pyridazine-7-carbonitrile (5); 3-(4-(isopropylamino)-5-(1-propyl-1H-pyrazol-4-yl)pyridin-2-yl)imidazo[1,2-b]pyridazine-7-carbonitrile (6); 2-(7-chloroimidazo[1,2-b]pyridazin-3-yl)-N-isopropyl-5-(1-(2,2,2-trifluoroethyl)-1H-pyrazol-4-yl)pyridin-4-amine (7); 3-(4-(isopropylamino)-5-(1-(2,2,2-trifluoroethyl)-1H-pyrazol-4-yl)pyridin-2-yl)imidazo[1,2-b]pyridazine-7-carbonitrile (8); 2-(7-chloroimidazo[1,2-b]pyridazin-3-yl)-N-(1-(2,2-difluoroethyl)-1H-pyrazol-4-yl)-5-(1-propyl-1H-pyrazol-4-yl)pyridin-4-amine (9); 3-(4-((1-(2,2-difluoroethyl)-1H-pyrazol-4-yl)amino)-5-(1-propyl-1H-pyrazol-4-yl)pyridin-2-yl)imidazo[1,2-b]pyridazine-7-carbonitrile (10); 2-(6-chloropyrazolo[1,5-a]pyrimidin-3-yl)-N-isopropyl-5-(4-propyl-1H-1,2,3-triazol-1-yl)pyridin-4-amine (11); 3-(4-(isopropylamino)-5-(4-propyl-1H-1,2,3- triazol-1-yl)pyridin-2-yl)pyrazolo[1,5-a]pyrimidine-6-carbonitrile (12); 4-(1-(6-(6-chloropyrazolo[1,5-a]pyrimidin-3-yl)-4-(isopropylamino)pyridin-3-yl)-H-1,2,3-triazol-4-yl)-2-methylbutan-2-ol (13); 4-(1-(6-(6-chloropyrazolo[1,5-a]pyrimidin-3-yl)-4-(oxetan-3-ylamino)pyridin-3-yl)-1H-1,2,3-triazol-4-yl)-2-methylbutan-2-ol (14); 3-(4-(isopropylamino)-5-(4-propyl-1H-1,2,3-triazol-1-yl)pyridin-2-yl) imidazo[1,2-b]pyridazine-7-carbonitrile (15); 3-(4-(isopropylamino)-5-(1-(tetrahydro-2H-pyran-4-yl)-1H-1,2,3-triazol-4-yl)pyridin-2-yl) imidazo[1,2-b]pyridazine-7-carbonitrile (16); 3-(5-(1-(1-acetylazetidin-3-yl)-1H-1,2,3-triazol-4-yl)-4-(isopropylamino)pyridin-2-yl) imidazo[1,2-b]pyridazine-7-carbonitrile (17); 3-(4-(cyclopropylamino)-5-(1-propyl-1H-1,2,3-triazol-4-yl)pyridin-2-yl)imidazo[1,2-b]pyridazine-7-carbonitrile (18); 2-(7-chloroimidazo[1,2-b]pyridazin-3-yl)-N-cyclopropyl-5-(1-propyl-1H-1,2,3-triazol-4-yl)pyridin-4-amine (19); 2-(7-chloroimidazo[1,2-b]pyridazin-3-yl)-N-isopropyl-5-(1-propyl-1H-1,2,3-triazol-4-yl)pyridin-4-amine (20); (3R)-methyl 4-(4-(6-(7-chloroimidazo[1,2-b]pyridazin-3-yl)-4-(cyclopropylamino)pyridin-3-yl)-1H-1,2,3-triazol-1-yl)-3-hydroxy-3-methylpiperidine-1-carboxylate (21); 3-(5-(4-(3-hydroxy-3-methylbutyl)-1H-1,2,3-triazol-1-yl)-4-(isopropylamino)pyridin-2-yl)imidazo[1,2-b]pyridazine-7-carbonitrile (22); 4-(1-(6-(6-chloropyrazolo[1,5-a]pyrimidin-3-yl)-4-((tetrahydro-2H-pyran-4-yl)amino)pyridin-3-yl)-1H-1,2,3-triazol-4-yl)-2-methylbutan-2-ol (23); 3-(4-((3,3-difluorocyclobutyl)amino)-5-(4-(3-hydroxy-3-methylbutyl)-1H-1,2,3-triazol-1-yl)pyridin-2-yl)pyrazolo[1,5-a]pyrimidine-6-carbonitrile (24); 3-(4-(((1S,3S)-3-fluorocyclopentyl)amino)-5-(4-(3-hydroxy-3-methylbutyl)-1H-1,2,3-triazol-1-yl)pyridin-2-yl)pyrazolo[1,5-a]pyrimidine-6-carbonitrile (25); 3-(5-(4-(3-hydroxy-3-methylbutyl)-1H-1,2,3-triazol-1-yl)-4-(oxetan-3-ylamino)pyridin-2-yl)pyrazolo[1,5-a]pyrimidine-6-carbonitrile (26); 3-(5-(1-(3-hydroxy-3-methylbutyl)-1H-pyrazol-4-yl)-4-(isopropylamino)pyridin-2-yl) imidazo[1,2-b]pyridazine-7-carbonitrile (27); 3-(4-(isopropylamino)-5-(5-(tetrahydro-2H-pyran-4-yl)-1H-pyrazol-3-yl)pyridin-2-yl)imidazo[1,2-b]pyridazine-7-carbonitrile (28); and 3-(5-(5-(3-hydroxy-3-methylbutyl)-1H-pyrazol-3-yl)-4-((tetrahydro-2H-pyran-4-yl)amino)pyridin-2-yl)pyrazolo[1,5-a]pyrimidine-6-carbonitrile (29).

One embodiment provides compounds of the Formula (I) having IRAK4 IC$_{50}$ values of ≤0.6 μM.

One embodiment provides compounds of the Formula (I) having IRAK4 IC$_{50}$ values of ≤0.1 μM.

One embodiment provides compounds of the Formula (I) having IRAK4 IC$_{50}$ values of ≤0.05 μM.

One embodiment provides compounds of the Formula (I) having IRAK4 IC$_{50}$ values of ≤0.025 μM.

One embodiment provides compounds of the Formula (I) having IRAK4 IC$_{50}$ values of ≤0.015 μM.

One embodiment provides compounds of the Formula (I) having IRAK4 IC$_{50}$ values of ≤0.01 μM.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The term "cyano" refers to the group —CN.
The term "amino" refers to the group —NH$_2$.
The term "oxo" refers to the group =O.
The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "C$_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "C$_{1-4}$ fluoroalkyl" is intended to include C$_1$, C$_2$, C$_3$, and C$_4$ alkyl groups substituted with one or more fluorine atoms. Representative examples of fluoroalkyl groups include, but are not limited to, —CF$_3$ and —CH$_2$CF$_3$.

The term "cyanoalkyl" includes both branched and straight-chain saturated alkyl groups substituted with one or more cyano groups. For example, "cyanoalkyl" includes —CH$_2$CN, —CH$_2$CH$_2$CN, and C$_{1-4}$ cyanoalkyl.

The term "hydroxyalkyl" includes both branched and straight-chain saturated alkyl groups substituted with one or more hydroxyl groups. For example, "hydroxyalkyl" includes —CH$_2$OH, —CH$_2$CH$_2$OH, and C$_{1-4}$ hydroxyalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "C$_{3-6}$ cycloalkyl" denotes cycloalkyl groups with three to six carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to IRAK4; or effective to treat or prevent autoimmune and/or inflammatory disease states, such as multiple sclerosis and rheumatoid arthritis; or effective to treat cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Utility

The compounds of the invention modulate kinase activity, including the modulation of IRAK-4. Other types of kinase activity that may be modulated by the compounds of the instant invention include, but are not limited to, the Pelle/IRAK family and mutants thereof.

Accordingly, compounds of Formula (I) have utility in treating conditions associated with the modulation of kinase activity, and particularly the selective inhibition of IRAK-4 activity or the inhibition of IRAK and other Pelle family kinases. Such conditions include TLR/IL-1 family receptor associated diseases in which cytokine levels are modulated as a consequence of intracellular signaling. Moreover, the compounds of Formula (I) have advantageous selectivity for IRAK-4 activity, preferably from at least 20 fold to over 1,000 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors IRAK-4, compounds of Formula (I) are useful in treating TLR/IL-1 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In one embodiment, the compounds of Formula (I) are useful in treating cancer, including Waldenstrom's Macroglobulinemia (WM), diffuse large B cell lymphoma (DLBCL), chronic lymphocytic leukemia (CLL), cutaneous diffuse large B cell lymphoma, and primary CNS lymphoma.

In addition, the kinase inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional IRAK-4-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

When the terms "IRAK-4-associated condition" or "IRAK-4-associated disease or disorder" are used herein, each is intended to encompass all of the conditions identified above as if repeated at length, as well as any other condition that is affected by IRAK-4 kinase activity.

The present invention thus provides methods for treating such conditions, comprising administering to a subject in need thereof a therapeutically-effective amount of at least one compound of Formula (I) or a salt thereof. "Therapeutically effective amount" is intended to include an amount of a compound of the present invention that is effective when administered alone or in combination to inhibit IRAK-4 and/or treat diseases.

The methods of treating IRAK-4 kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit IRAK-4 and/or treat diseases associated with IRAK-4.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IRAK-4 kinase-associated conditions, including TLR and IL-1 family receptor mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended.

The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, *arachis* oil; olive oil; sesame oil; and coconut oil; or in mineral oil, such as, for example, liquid paraffin.

An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular disorder, diuresis, and/or natriuresis. In another embodiment, the package insert states that the pharmaceutical composition can be used in combination (as defined previously) with a second therapeutic agent to treat cardiovascular disorder, diuresis, and/or natriuresis. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, or other written sheet that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic) on which the desired information has been formed (e.g., printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The reactions and techniques described in this section are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Compound of the general formula I can be prepared according to the methods outlined in the following schemes. For example, in Scheme 1, the bromide 1.1 may be reacted with XXX to form the chlorotraizole 1.2. Subsequent reaction with various heterocyclic cross coupling reagents, such as heterocyclic stannanes or boronic acid derivatives, in the presence of a metal catalyst can provide compounds such as 1.3.

SCHEME 1

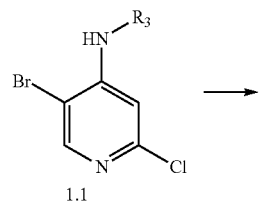

1.1

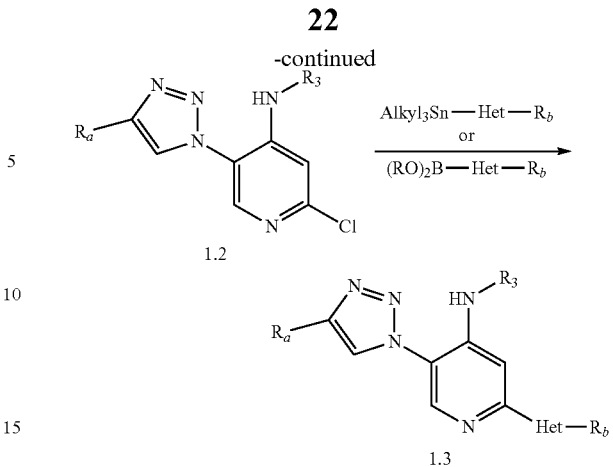

Scheme 2 demonstrates an alternative sequence of steps to obtain compounds of the general formula. Starting with bromide 1.1, alternative heterocycles, such as pyrazoles can be coupled using standard cross coupling methods. These methods can utilize heterocyclic boronic acids or stannanes, among others, to provide intermediates of the formula 2.1. Subsequent coupling with additional functionalized heterocycles can lead to compounds such as the general formula 2.2. Other functionalized heterocycles can be substituted at the first step. For example, an appropriately substituted imidazole can replace the pyrazole in Scheme 2. An alternative sequence to compounds such as 2.2 may start from the iodide 2.3. Alkylation of the C4 amine may afford compounds of the formula 2.4, which upon reaction with various heterocyclic cross coupling reagents, may form compounds such as 2.1. Intermediates 2.1 may be processed to 2.2 as previously described.

SCHEME 2

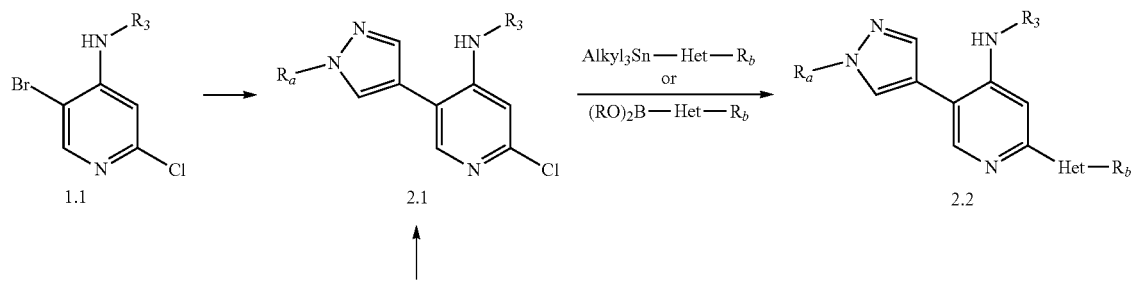

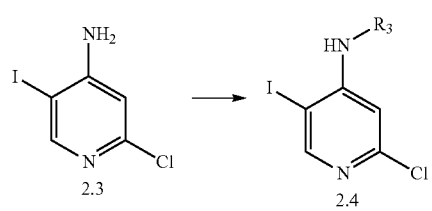

Another variation of the synthesis of these molecules is shown in Scheme 3. Reacting the amine 3.1 with an appropriate amine, such as isopropyl amine, can provide compound 3.2. Treatment of 3.2 with a reducing reagent, such as LAH may provide the alcohol 3.3 which can be converted to the aldehyde 3.4 with an appropriate oxidizing reagent. The aldehyde 3.4 may be converted to the alkyne using a base and dimethyl (1-diazo-2-oxopropyl)phosphonate in a solvent such as methanol. Treatment of 3.5 with an alkyl azide in the presence of a metal, such as copper, may afford triazolo pyridines such as 3.6. The chloride of 3.6 may be converted to an alkyl stannane with hexamethylditin and a palladium catalyst to afford 3.7. Reaction of 3.7 with a variety of heterocyclic halides may provide compounds of the formula 3.8.

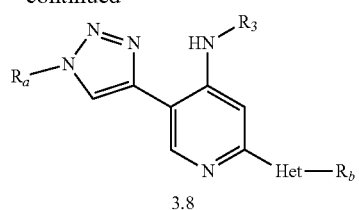

An additional variation in the preparation of these compounds is shown in Scheme 4. The acid 4.1, using standard transformations known to one skilled in the art, can be transformed to the ketone 4.2. Reaction of the ketone with a carbonyl containing group, such as an anhydride, can for the di-ketone 4.3. Reaction of 4.3 with a reagent such as hydrazine can form the pyrazole ring shown in compound 4.4. An appropriately substituted pyrazole (Ra equals a reactive functional group such as an ester) can be further transformed using standard chemical manipulations. Conversion of the chloride in compound 4.4 to a stannane such as 4.5, or other function group such as a boron derivative would provide useful compounds to allow for the conversion to 4.6. Compounds 4.6 can be prepared using various cross coupling protocols, such a Stille coupling, in the presence of a catalyst, such as palladium.

SCHEME 3

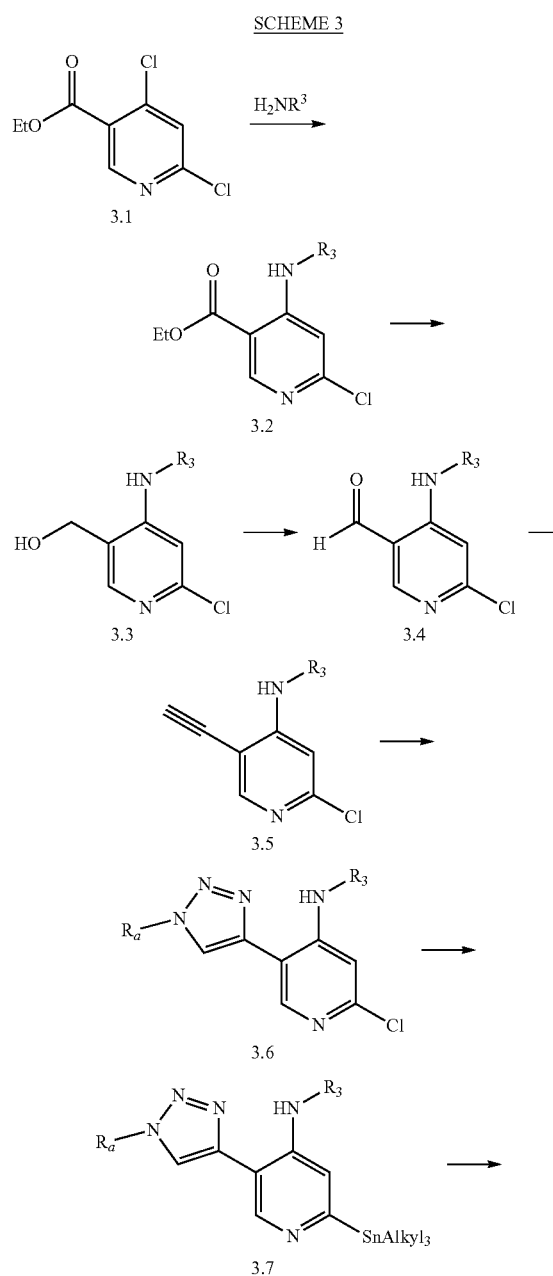

SCHEME 4

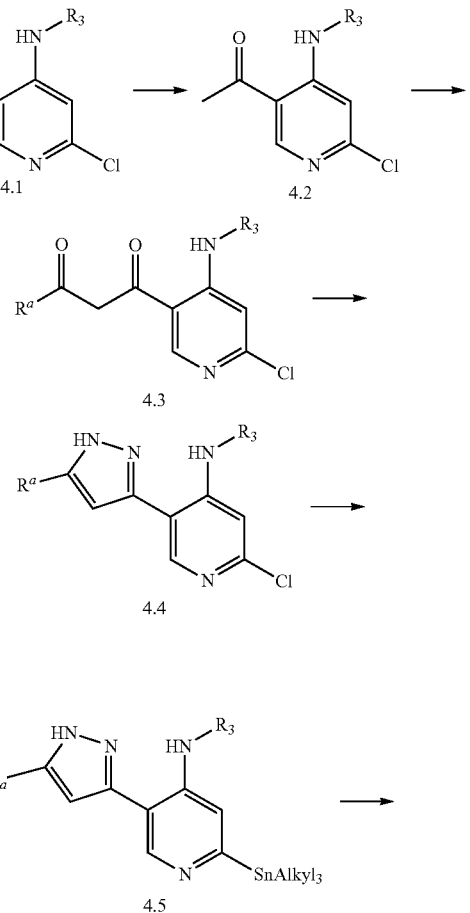

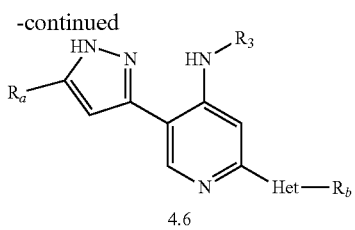

4.6

EXAMPLES

Compounds of the current invention, and intermediates used in the preparation of compounds of the current invention, can be prepared using procedures shown in the following examples and related procedures. The methods and conditions used in these examples, and the actual compounds prepared in these examples, are not meant to be limiting, but are meant to demonstrate how the compounds of the current invention can be prepared. Starting materials and reagents used in these examples, when not prepared by a procedure described herein, are generally either commercially available, or are reported in the chemical literature, or may be prepared by using procedures described in the chemical literature. The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather defined by the claims appended hereto.

In the examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being Column chromatography was performed with pre-packed silica gel cartridges using an Isco medium pressure chromatography apparatus (Teledyne Corporation), eluting with the solvent or solvent mixture indicated. Preparative high performance liquid chromatography (HPLC) was performed using a reverse phase column (Waters Sunfire $C_{18}$, Waters Xbridge $C_{18}$, PHENOMENEX® Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chemical names were determined using ChemDraw Ultra, version 9.0.5 (CambridgeSoft). The following abbreviations are used:
aq. aqueous
BISPIN bis(pinacolato)diboron
brine saturated aqueous sodium chloride
DCM dichloromethane
DMA N,N-dimethylacetamide
DMF N,N-dimethylformamide
DMSO dimethyl sulfoxide
DPPF 1,1'-bis(diphenylphosphino)ferrocene
EtOAc ethyl acetate
EtOH ethanol
g gram(s)
h hour(s)
HPLC High Performance Liquid Chromatography
KOAc potassium acetate
LAH lithium aluminum hydride
LCMS Liquid Chromatography-Mass Spectroscopy
MeCN acetonitrile
MeMgBr methyl magnesium bromide
MeOH methanol
MPLC medium pressure liquid chromatography
MTBE methyl t-butyl ether
NBS N-bromosuccinimide
$NH_4OAc$ ammonium acetate
NIS N-iodosuccinimide
$Pd_2(dba)_3$ tris-(dibenzylideneacetone)dipalladium
pet ether petroleum ether
t-BuOH tert-butanol
TFA trifluoroacetic acid
THF tetrahydrofuran
HPLC Conditions:

A. Sunfire C18 (3×150 mm), 3.5 micron, mobile phase A: 95:5 water/MeCN, 0.05% TFA; mobile phase B: 95:5 MeCN/water, 0.05% TFA; 1 mL/min, 12 min gradient.

B. Xbridge Phenyl (3×150 mm), 3.5 micron, mobile phase A: 95:5 water/MeCN, 0.05% TFA; mobile phase B: 95:5 MeCN/water, 0.05% TFA; 1 mL/min, 12 min gradient.

C. Waters Acquity UPLC BEH C18 column (2.1×50 mm), mobile phase A: 5:95 MeCN/10 mM aq. ammonium acetate; mobile phase B: 95:5 10 mM aq. ammonium acetate/MeCN; Gradient 0-100% B over 3 minutes, then 0.75 min hold @ 100% B; 50° C. column temperature D. Waters Acquity UPLC BEH C18 column (2.1×50 mm), mobile phase A: 5:95 MeCN/0.1% TFA; mobile phase B: 95:5 0.1% TFA/MeCN; Gradient 0-100% B over 3 minutes, then 0.75 min hold @ 100% B; 50° C. column temperature E. Ascentis Express C18 (2.1×50 mm), 2.7 micron, mobile phase A: 98:2 water/MeCN, 10 mM $NH_4OAc$; mobile phase B: 2:98 water/MeCN, 10 mM $NH_4OAc$; 1.1 mL/min, 3 min gradient F. Ascentis Express C18 (2.1×50 mm), 2.7 micron, mobile phase A: 95:5 water/MeCN, 0.01% TFA; mobile phase B: 5:95 water/MeCN, 0.01% TFA; 1.1 mL/min, 3 min gradient G. Xbridge Phenyl (4.6×150 mm), 3.5 micron, mobile phase A: 95:5 water/MeCN, 0.05% TFA; mobile phase B: 95:5 MeCN/water, 0.05% TFA; 1 mL/min, 18 min gradient.

Example 1

3-(5-(4-(2-hydroxypropan-2-yl)-1H-pyrazol-1-yl)-4-(isopropylamino)pyridin-2-yl) pyrazolo[1,5-a]pyrimidine-6-carbonitrile

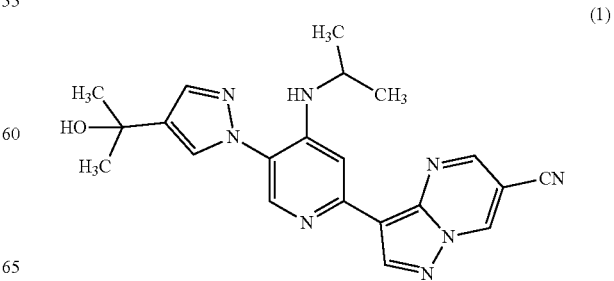

Intermediate 1A: Ethyl 1-(6-chloro-4-(isopropylamino)pyridin-3-yl)-1H-pyrazole-4-carboxylate

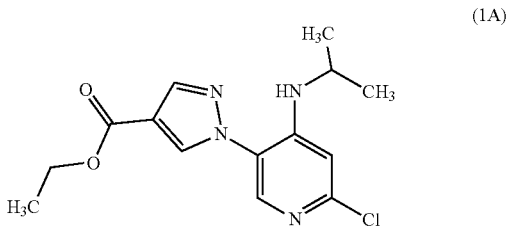 [SMILES: CCOC(=O)c1cnn(-c2cnc(Cl)cc2NC(C)C)c1]

(1A)

To a stirred solution of 2-chloro-5-iodo-N-isopropylpyridin-4-amine (400 mg, 1.35 mmol) in 1,4-dioxane (10 mL) was added ethyl 1H-pyrazole-4-carboxylate (189 mg, 1.35 mmol), CuI (51 mg, 0.27 mmol), $K_2CO_3$ (373 mg, 2.7 mmol) and trans-N,N'-dimthylcyclohexane-1,2-diamine (115 mg, 0.81 mmol). The mixture was sealed and heated at 110° C. for 14 hours. The solvents were removed and the mixture was partition between EtOAc and water. The organic layer was dried over $Na_2SO_4$, filtered, and concentrated. The product was purified via column chromatography (15% EtOAc/pet ether to afford ethyl 1-(6-chloro-4-(isopropylamino)pyridin-3-yl)-1H-pyrazole-4-carboxylate (300 mg, 72% yield). LCMS 309.4 (M+H).

Intermediate 1B: 2-(1-(6-chloro-4-(isopropylamino)pyridin-3-yl)-1H-pyrazol-4-yl) propan-2-ol

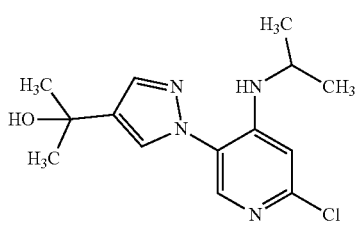

(1B)

To a stirred solution of ethyl 1-(6-chloro-4-(isopropylamino)pyridin-3-yl)-1H-pyrazole-4-carboxylate (220 mg, 0.72 mmol) in THF (10 mL) at 0° C. was added MeMgBr (0.71 mL, 2.14 mmol). The reaction mixture was stirred at room temperature for 1 h then quenched with saturated aqueous $NH_4Cl$. The solvents were removed and the mixture was partition between EtOAc and water. The organic layer was dried over $Na_2SO_4$, filtered, and concentrated. The product was purified via column chromatography (15% EtOAc/pet ether to afford 2-(1-(6-chloro-4-(isopropylamino)pyridin-3-yl)-1H-pyrazol-4-yl)propan-2-ol (45 mg, 30% yield). LCMS 295.4 (M+H).

Intermediate 1C: 3-Bromopyrazolo[1,5-a]pyrimidine-6-carbonitrile

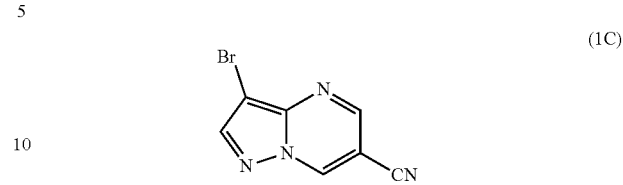

(1C)

To a stirred solution of pyrazolo[1,5-a]pyrimidine-6-carbonitrile (0.7 g, 4.86 mmol) in MeCN (20 mL) was added NBS (0.86 g, 4.86 mmol). The reaction mixture was then stirred for 3 hours at 25° C. The reaction mixture was diluted with water and extracted with EtOAc (3×). The organic layer was dried over $Na_2SO_4$, filtered, and concentrated. The product was purified via column chromatography (33% EA/H) to afford 3-bromopyrazolo[1,5-a]pyrimidine-6-carbonitrile (0.94 g, 78% yield) as an amber solid. $^1$H-NMR (400 MHz, $CDCl_3$) δ 9.05 (s, 1H), 8.66 (s, 1H), 8.34 (s, 1H); LCMS 221.1 (M+H).

Intermediate 1D: 3-(4,4,5,5-tetramethyl-1,3,2-dioxaborolan-2-yl)pyrazolo[1,5-a]pyrimidine-6-carbonitrile

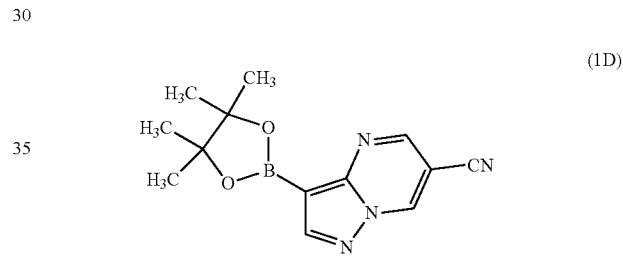

(1D)

To a stirred solution of 3-bromopyrazolo[1,5-a]pyrimidine-6-carbonitrile (250 mg, 1.121 mmol) in 1,4-dioxane (10 mL) was added KOAc (220 mg, 2.242 mmol) and BISPIN (1139 mg, 4.48 mmol) and degassed for 20 mins with nitrogen then added bis(triphenylphosphine)Pd(II)$Cl_2$ (39.3 mg, 0.056 mmol). The reaction mixture was heated to 110° C. for 16 hrs. The reaction mixture was cooled and filtered through celite and washed with pentane. The filtrate was concentrated under reduced pressure to afford crude compound as a gummy compound. The residue was triturated with pentane and the solids obtained were washed with pentane to afford 3-(4,4,5,5-tetramethyl-1,3,2-dioxaborolan-2-yl)pyrazolo[1,5-a]pyrimidine-6-carbonitrile (150 mg, 50% yield).

Example 1

To a stirred solution of 2-(1-(6-chloro-4-(isopropylamino)pyridin-3-yl)-1H-pyrazol-3-yl)propan-2-ol (40 mg, 0.14 mmol) and 3-(4,4,5,5-tetramethyl-1,3,2-dioxaborolan-2-yl)pyrazolo[1,5-a]pyrimidine-6-carbonitrile (73 mg, 0.27 mmol) in 1,4-dioxane (2 mL) was added KOAc (40 mg, 0.407 mmol). The mixture was degassed with $N_2$ for 5 min then tetrakistriphenylphosphine Pd(0) (31 mg, 0.027 mmol) was added. The mixture was further degassed for 5 min, and then heated at 120° C. for 1 hour under microwave irradiation. The mixture was cooled, filtered, and concentrated. The product was purified via preparative TLC (5% MeOH/DCM) to afford 3-(5-(4-(2-hydroxypropan-2-yl)-1H-pyrazol-1-yl)-4-(isopropyl amino)pyridin-2-yl)pyrazolo[1,5-a]pyrimidine-6-carbonitrile (8 mg, 14% yield). $^1$H-NMR (400 MHz, MeOD-d$_4$) δ 9.70 (s, 1H), 8.94 (s, 1H), 8.85 (s, 1H), 8.2 (s, 1H), 8.00 (s, 1H), 7.95 (s, 1H), 7.81 (s, 1H), 3.90 (m, 1H), 1.61 (s, 6H), 1.31 (s, 3H), 1.25 (s, 3H); LCMS 403.5 (M+H); HPLC rt 12.9 min, Conditions G.

Example 2

2-(7-chloroimidazo[1,2-b]pyridazin-3-yl)-N-isopropyl-5-(4-(tetrahydro-2H-pyran-4-yl)-1H-pyrazol-1-yl)pyridin-4-amine

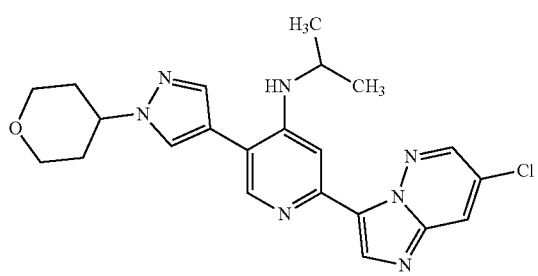

(2)

Intermediate 2A: 2-Chloro-5-iodopyridin-4-amine

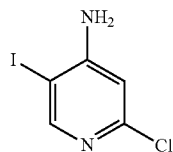

(2A)

To a stirred solution of 2-chloropyridin-4-amine (5 g, 39 mmol) in DMF (50 mL) was added NIS (8.75 g, 39 mmol). The reaction mixture was then heated at 80° C. for 3 h. The mixture was cooled and the DMF removed in vacuo. The residue was partitioned between EtOAc and water and the layers were separated. The organic layer was dried over Na$_2$SO$_4$, filtered, and concentrated. The product was purified via column chromatography (10% EtOAc/pet ether) to afford 2-chloro-5-iodopyridin-4-amine (4 g, 39% yield). $^1$H NMR (400 MHz, DMSO-d$_6$) δ 8.20 (s, 1H), 6.64 (s, 1H), 6.50 (br s, 2H); LC/MS: 254.8 (M+). Further elution with 12% EtOAc/pet ether afforded 2-chloro-3-iodopyridin-4-amine (4 g, 39% yield).

Intermediate 2B: 2-Chloro-5-iodo-N-isopropylpyridin-4-amine

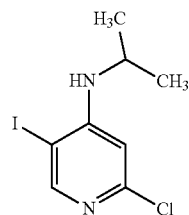

(2B)

To a stirred solution of 2-chloro-5-iodopyridin-4-amine g, 5.7 mmol) in DMF (40 mL), was added NaH (2.26 g, 47.2 mmol) at 0° C. The mixture was allowed to warm to room temperature and then was heated at 80° C. 2-Iodopropane (3.14 mL, 31.4 mmol) in 4 mL of DMF was added drop wise and heating continued for 4 hours. The mixture was cooled to room temperature and quenched with crushed ice. The product was extracted with DCM (2×20 mL) and the organic layer was dried over Na$_2$SO$_4$, filtered, and concentrated. Purification via column chromatography (10% EA/pet ether) afforded 2-chloro-5-iodo-N-isopropylpyridin-4-amine (2.8 g, 60% yield) as a colorless liquid. $^1$H NMR (400 MHz, DMSO-d$_6$) δ 8.23 (S, 1H), 6.61 (s, 1H), 5.34 (d, J=8.0 Hz, 1H), 3.80 (m, 1H), 1.21 (s, 3H), 1.19 (s, 3H); LC/MS: 296.6 (M$^+$).

Intermediate 2C: 2-Chloro-N-isopropyl-5-(1H-pyrazol-4-yl)pyridin-4-amine

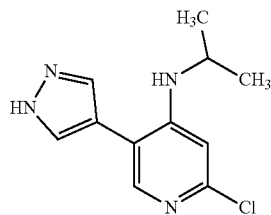

(2C)

To a stirred solution of 2-chloro-5-iodo-N-isopropylpyridin-4-amine (500 mg, 1.7 mmol) in DMF (10 mL) and water (1 mL) was added tert-butyl 4-(4,4,5,5-tetramethyl-1,3,2-dioxaborolan-2-yl)-1H-pyrazole-1-carboxylate (496 mg, 1.7 mmol) and K$_2$CO$_3$ (700 mg, 5.06 mmol). The mixture was degassed via nitrogen bubble for 2 min and 2nd generation Xphos precatalyst (133 mg, 0.169 mmol) was added and the degassing was continued for another 2 mins. The mixture was sealed and heated at 100° C. for 3 h. The reaction mixture was cooled and concentrated. EtOAc (150 mL) was added and the organic layer was washed with ice cold water (2×20 mL). The organic layer was dried over Na$_2$SO$_4$, filtered and concentrated. The product was purified via column chromatography (30% EtOAc/pet ether) to afford 2-chloro-N-isopropyl-5-(1H-pyrazol-4-yl)pyridin-4-amine (250 mg, 63% yield). LC/MS: 236.9 (M+).

Intermediate 2D: 2-Chloro-N-isopropyl-5-(1-(tetrahydro-2H-pyran-4-yl)-1H-pyrazol-4-yl)pyridin-4-amine

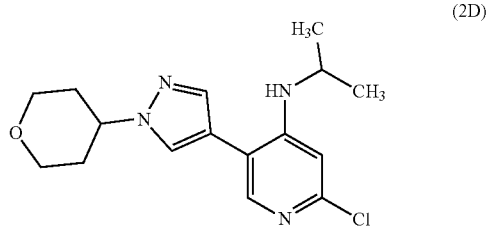 [SMILES: CC(C)Nc1cc(Cl)ncc1-c1cnn(C2CCOCC2)c1]

(2D)

To a stirred solution of 2-chloro-N-isopropyl-5-(1H-pyrazol-4-yl)pyridin-4-amine (200 mg, 0.845 mmol) in DMF (4 mL) was added $Cs_2CO_3$ (413 mg, 1.27 mmol) and 4-bromotetrahydro-2H-pyran (167 mg, 1.01 mmol). The reaction mixture was heated at 160° C. for 2.5 h under microwave irradiation. After cooling, the mixture was concentrated to dryness and then partitioned between EtOAc (150 mL) and ice water (20 mL). The layers were separated and the organic layer washed again with cold water. The organic layer was dried over $Na_2SO_4$, filtered, and concentrated. The product was purified via column chromatography (30% EtOAc/pet ether) to afford 2-chloro-N-isopropyl-5-(1-(tetrahydro-2H-pyran-4-yl)-1H-pyrazol-4-yl)pyridin-4-amine (80 mg, 30% yield). LCMS 321.1 (M+H).

Intermediate 2E: N-Isopropyl-5-(1-(tetrahydro-2H-pyran-4-yl)-1H-pyrazol-4-yl)-2-(trimethylstannyl)pyridin-4-amine

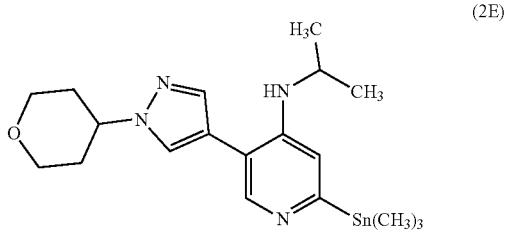

(2E)

To a stirred solution of 2-chloro-N-isopropyl-5-(1-(tetrahydro-2H-pyran-4-yl)-1H-pyrazol-4-yl)pyridin-4-amine (70 mg, 0.218 mmol) in 1,4-dioxane (10 mL) was added hexamethylditin (0.090 mL, 0.436 mmol). 1,1'-Bis(di-tert-butylphosphine) ferrocene palladium dichloride (7.1 mg, 10.9 µmol) was added and the mixture was degassed for 5 min. The reaction mixture was heated at 115° C. for 3 hours in a sealed tube. The reaction mixture was filtered through celite, and washed with 20 mL of ethyl acetate. The filtrate was concentrated to get N-isopropyl-5-(1-(tetrahydro-2H-pyran-4-yl)-1H-pyrazol-4-yl)-2-(trimethylstannyl)pyridin-4-amine (90 mg, 92% yield) which was used without further purification.

Intermediate 2F: 7-Chloroimidazo[1,2-b]pyridazine

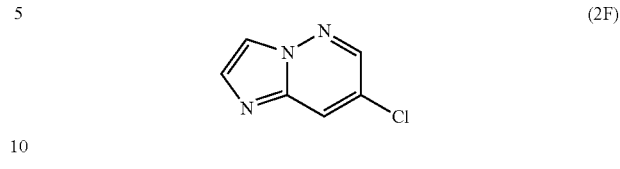

(2F)

A solution of 5-chloropyridazin-3-amine (14.4 g, 111 mmol) and chloroacetaldehyde (81 mL, 556 mmol) in 2-propanol (150 mL) was heated at 100° C. for 16 h. The mixture was cooled to room temperature and concentrated. The residue was added water (400 mL) and washed with EtOAc (3×500 mL). The aqueous layer was taken to pH~8 with saturated $NaHCO_3$ solution and was extracted with EtOAc (3×50 mL). The combined organic layers were washed with brine, dried over $Na_2SO_4$, filtered and concentrated. The material was purified via column chromatography (40% EtOAc/PE) to obtain 7-chloroimidazo[1,2-b]pyridazine (10.2, 59% yield) as a brown solid. $^1$H NMR: (400 MHz, $CDCl_3$) δ 8.27 (s, 1H), 7.96 (s, 2H), 7.78 (s, 1H); LCMS 154.3 (M+H).

Intermediate 2G: 7-Chloro-3-iodoimidazo[1,2-b]pyridazine

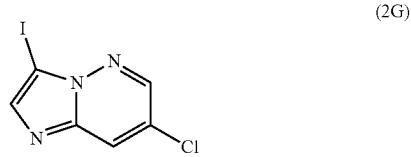 [SMILES: Clc1cnn2c(I)cnc2c1]

(2G)

To a stirred solution of 7-chloroimidazo[1,2-b]pyridazine (250 mg, 1.63 mmol) in DMF (10 mL) was added NIS (733 mg, 3.26 mmol) and the reaction mixture was stirred for 3 hours. The mixture was concentrated to dryness then partitioned between EtOAc (100 mL) and ice water (30 mL). The layers were separated and the organic layer washed again with cold water. The organic layer was dried over $Na_2SO_4$, filtered, and concentrated. The product was purified via column chromatography (20% EtOAc/pet ether) to afford 7-chloro-3-iodoimidazo[1,2-b]pyridazine (390 mg, 77% yield). $^1$H NMR (400 MHz, DMSO-$d_6$) δ 8.77 (s, 1H), 8.45 (s, 1H), 7.90 (s, 1H); LCMS 279.9 (M$^+$).

Example 2

To a stirred solution of N-isopropyl-5-(1-(tetrahydro-2H-pyran-4-yl)-1H-pyrazol-4-yl)-2-(trimethylstannyl)pyridin-4-amine (45 mg, 0.100 mmol) and 7-chloro-3-iodoimidazo[1,2-b]pyridazine (28.0 mg, 0.100 mmol) in 1,4-dioxane (10 mL) was added CuI (1.91 mg, 10 µmol). The mixture was degassed with $N_2$ for 5 min then tetrakistriphenylphosphine Pd(0) (12 mg, 0.00 mmol) was added. The mixture was further degassed for 5 min then heated at 110° C. for 15 hours in a sealed tube. The mixture was cooled, filtered through celite and rinsed. The filtrates were concentrated and partitioned between DCM and 1.5N HCl. The aqueous layer was washed with DCM and then treated with $NaHCO_3$. The product was extracted into EtOAc and purified via preparative HPLC to afford 2-(7-chloroimidazo[1,2-b]

pyridazin-3-yl)-N-isopropyl-5-(1-(tetrahydro-2H-pyran-4-yl)-1H-pyrazol-4-yl)pyridin-4-amine (7 mg, 17% yield). $^1$H NMR: (400 MHz, DMSO-d$_6$) δ 8.85 (d, J=2.0 Hz, 1H), 8.56 (d, J=2.5 Hz, 1H), 8.38 (s, 1H), 8.21 (s, 1H), 8.14 (s, 1H), 7.86 (s, 1H), 7.78 (s, 1H), 5.21 (d, J=7.5 Hz, 1H), 4.48 (br. s., 1H), 4.00 (d, J=11.5 Hz, 2H), 3.79 (br. s., 1H), 3.57-3.43 (m, 2H), 2.10-1.94 (m, 4H), 1.27 (d, J=6.5 Hz, 6H); LCMS 438.3 (M+H), HPLC rt 1.61 min, conditions E.

The Examples in Table 1 were prepared using the general methods outlined for Example 2 using the appropriate starting material.

TABLE 1

| Ex. No. | Structure | HPLC rt (min) | HPLC cond. | LCMS |
|---------|-----------|---------------|------------|------|
| 3 | 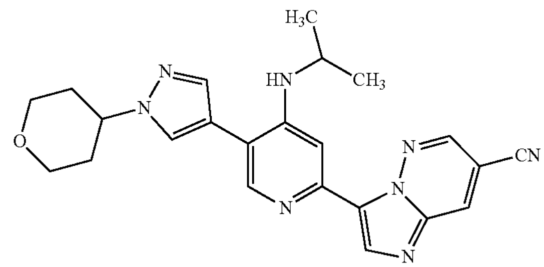 [SMILES: CC(C)Nc1cc(-c2cnc3cc(C#N)cnn23)ncc1-c1cnn(C2CCOCC2)c1] | 1.46 | E | 429.3 |
| 4 | 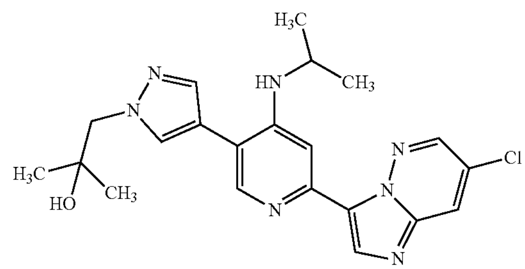 [SMILES: CC(C)Nc1cc(-c2cnc3cc(Cl)cnn23)ncc1-c1cnn(CC(C)(C)O)c1] | 1.51 | E | 426.3 |
| 5 | 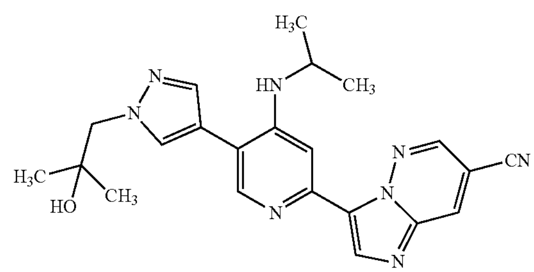 [SMILES: CC(C)Nc1cc(-c2cnc3cc(C#N)cnn23)ncc1-c1cnn(CC(C)(C)O)c1] | 1.36 | E | 417.3 |
| 6 | 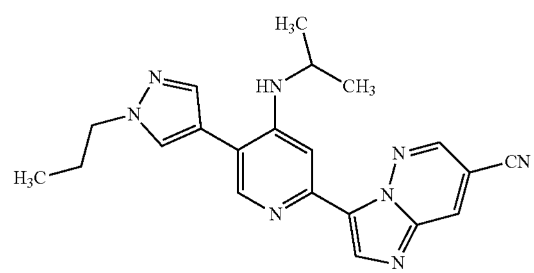 [SMILES: CCCn1cc(-c2cnc(-c3cnc4cc(C#N)cnn34)cc2NC(C)C)cn1] | 1.64 | E | 387.3 |
| 7 | 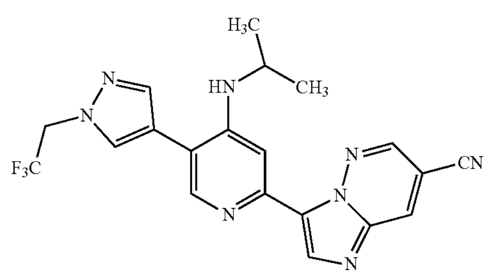 [SMILES: CC(C)Nc1cc(-c2cnc3cc(C#N)cnn23)ncc1-c1cnn(CC(F)(F)F)c1] | 1.71 | E | 436.2 |

TABLE 1-continued

| Ex. No. | Structure | HPLC rt (min) | HPLC cond. | LCMS |
|---|---|---|---|---|
| 8 | 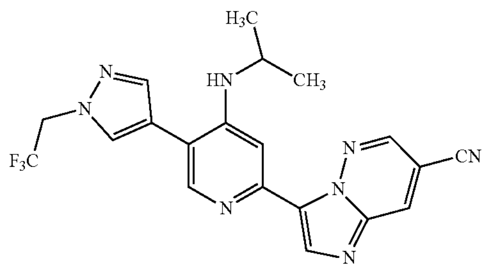 [SMILES: CC(C)Nc1cc(-c2cnc3cc(C#N)cnn23)ncc1-c1cnn(CC(F)(F)F)c1] | 1.54 | E | 427.2 |
| 9 | 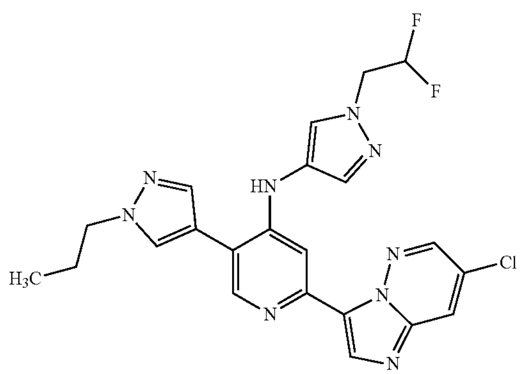 [SMILES: CCCn1cc(-c2cnc(-c3cnc4cc(Cl)cnn34)cc2Nc2cnn(CC(F)F)c2)cn1] | 1.73 | E | 484.1 |
| 10 | 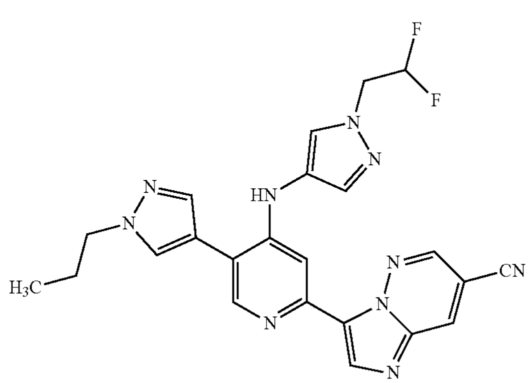 [SMILES: CCCn1cc(-c2cnc(-c3cnc4cc(C#N)cnn34)cc2Nc2cnn(CC(F)F)c2)cn1] | 1.65 | E | 475.2 |

Example 11

2-(6-chloropyrazolo[1,5-a]pyrimidin-3-yl)-N-isopropyl-5-(4-propyl-1H-1,2,3-triazol-1-yl)pyridin-4-amine

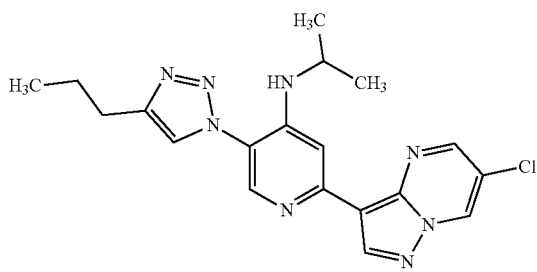
(11)

Intermediate 11A:
5-Bromo-2-chloro-N-isopropylpyridin-4-amine

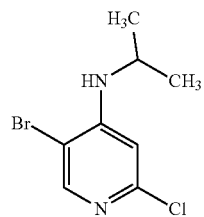
(11A)

To a stirred solution of 5-bromo-2,4-dichloropyridine (3.0 g, 13.22 mmol), isopropylamine (1.7 mL, 19.83 mmol), and Hunig's Base (11.6 mL, 66.1 mmol) in DMF (5 mL) at room temperature was then heated at 120° C. behind a safety shield for 4 hours, at which point it was judged to be complete by LCMS. The reaction mixture was diluted with ethyl acetate and washed 10% LiCl (3×). The organic layer was dried over Na$_2$SO$_4$, filtered and concentrated to afford the crude product. The product was purified by column chromatography (hexanes/EtOAc) to afford 5-bromo-2-chloro-N-isopropylpyridin-4-amine (1.29 g, 37% yield) as a colorless oil. LCMS m/z 249.0 (M+H).

Intermediate 11B: 2-chloro-N-isopropyl-5-(4-propyl-1H-1,2,3-triazol-1-yl)pyridin-4-amine

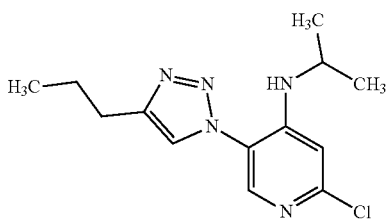
(11B)

To a stirred suspension of 5-bromo-2-chloro-N-isopropylpyridin-4-amine (100 mg, 0.401 mmol), sodium azide (52.1 mg, 0.801 mmol), sodium ascorbate (7.94 mg, 0.040 mmol), N1,N2-dimethylethane-1,2-diamine (10.60 mg, 0.120 mmol) in ethanol (1.4 ml) and H$_2$O (0.600 ml) at room temperature was bubbled nitrogen for 5 minutes then copper (I) iodide (15.26 mg, 0.080 mmol) and pent-1-yne (136 mg, 2.0 mmol) were added. The reaction mixture was heated at 90° C. for 2 hours, cooled to 25° C. and added another set of reagents as above. Heating was continued for 16 hours at which point it was judged to be complete by LCMS. The reaction mixture was diluted with ethyl acetate (2 mL), filtered, and concentrated in vacuo. Purified by MPLC (hexanes/EtOAc) to afford 2-chloro-N-isopropyl-5-(4-propyl-1H-1,2,3-triazol-1-yl)pyridin-4-amine (46 mg, 37% yield). LCMS 252.2 (M-N2)$^+$.

Intermediate 11C: 3-Bromo-6-chloropyrazolo[1,5-a]pyrimidine

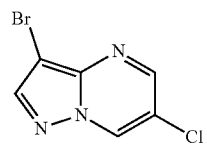
(11C)

To a stirred solution of 6-chloropyrazolo[1,5-a]pyrimidine (0.3 g, 1.954 mmol) in DCM (10 mL) was added NBS (0.348 g, 1.954 mmol) at 0° C. The reaction mixture was stirred for 5 h at the same temperature. The mixture was diluted with water and extracted with ethyl acetate (3×15 mL). The combined organic layers were dried over anhydrous Na$_2$SO$_4$ and evaporated under reduced pressure to get the crude compound. The crude compound was taken to the next step without further purification. LCMS m/z 231.8 (M+H); $^1$H NMR (300 MHz, DMSO-d$_6$) δ 9.63 (d, J=2.3 Hz, 1H), 8.70 (d, J=2.3 Hz, 1H), 8.43 (s, 1H).

Intermediate 11D: 6-Chloro-3-(4,4,5,5-tetramethyl-1,3,2-dioxaborolan-2-yl)pyrazolo[1,5-a]pyrimidine

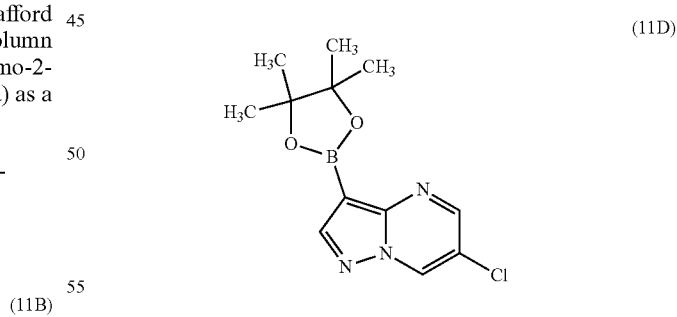
(11D)

To a solution of 3-bromo-6-chloropyrazolo[1,5-a]pyrimidine (2.0 g, 8.6 mmol) in 1,4-dioxane (100 mL) was added 4,4,4',4',5,5,5',5'-octamethyl-2,2'-bi(1,3,2-dioxaborolane) (5.46 g, 21.5 mmol) followed by potassium acetate (2.53 g, 25.8 mmol) and the solution was degassed for 5 min with nitrogen. To this reaction mixture, 1,1'-bis(diphenylphosphino)ferrocene-palladium(II)dichloride dichloromethane complex (0.35 g, 0.43 mmol) was added and the mixture was degassed for another 15 min. The reaction vessel was sealed and heated to 100° C. for 18 h. The reaction mixture was filtered through a celite bed and washed with 3; 2 EtOAc/pet ether. The filtrate was concentrated under reduced pressure. The crude compound was used as is 6-chloro-3-(4,4,5,5-tetramethyl-1,3,2-dioxaborolan-2-yl)pyrazolo[1,5-a]pyrimidine (1.2 g, 50% yield) as a brown solid $^1$H NMR (400 MHz, DMSO-d$_6$) δ 9.63 (d, J=2.0 Hz, 1H), 8.74 (d, J=2.5 Hz, 1H), 8.37 (s, 1H), 1.31 (s, 13H); LCMS m/z 198.0 (M+H).

Intermediate 11E:
Imidazo[1,2-b]pyridazine-7-carbonitrile

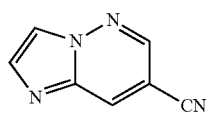

(11E)

A mixture of 7-chloroimidazo[1,2-b]pyridazine (21 g, 137 mmol) and DMA (420 mL) in a 1 L bottle was purged with N$_2$ for 5 min. Zinc cyanide (24.08 g, 205 mmol) and zinc (1.788 g, 27.3 mmol) were added and the bottle was purged with N$_2$ for 5 min. DPPF (15.16 g, 27.3 mmol) and Pd$_2$(dba)$_3$ (12.52 g, 13.67 mmol) were added and the reaction mixture was heated at 130° C. for 12 hrs. The reaction mixture was cooled to room temperature, filtered through celite, and washed with ethyl acetate. The solvents were removed and the residue was partitioned between EtOAc and water. The layers were separated and the organic layer was concentrated. MTBE (250 mL) was added and the resulting solids were stirred well and filtered to afford 21 g of a brown solid which was purified via column chromatography (60-70% EtOAc/pet ether) to afford imidazo[1,2-b]pyridazine-7-carbonitrile (12.8 g, 65% yield) as a slight brown solid. $^1$H NMR (300 MHz, DMSO-d$_6$) δ 8.98 (s, 1H), 8.89 (s, 1H), 8.60 (s, 1H), 8.10 (s, 1H); LCMS m/z 145.0 (M+H).

Intermediate 11F: 3-Bromoimidazo[1,2-b]pyridazine-7-carbonitrile

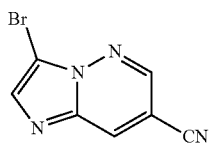

(11F)

A solution of imidazo[1,2-b]pyridazine-7-carbonitrile (25 g, 173 mmol) in MeCN (500 mL) was prepared in a 2 L 4-necked round bottom flask. The contents were cooled to 0-5° C. and a solution of NBS (32.4 g, 182 mmol) in MeCN (250 mL) was added dropwise over 30 mins. After addition, the reaction mixture was slowly brought to 25-30° C. and stirred for 2 hours. The reaction mixture was concentrated under vacuum at 50-55° C. and the crude residue was added water (250 mL) and stirred for 10 min. The resulting solids were collected and rinsed with water. The solid was slurried in MTBE (150 mL), stirred for about 10 mins, filtered, and washed with fresh MTBE (100 mL) and dried on the filter. The material was purified via column chromatography (30-50% ethyl acetate in Pet-ether) to afford, after slurrying again in MTBE (100 mL) 3-bromoimidazo[1,2-b]pyridazine-7-carbonitrile (18 g, 46% yield). $^1$H NMR (400 MHz, DMSO-d$_6$) δ 9.03 (m, 2H), 8.25 (s, 1H); LCMS m/z 225.0 (M+2H).

Example 11

2-Chloro-N-isopropyl-5-(4-propyl-1H-1,2,3-triazol-1-yl)pyridin-4-amine (30 mg, 0.107 mmol) was dissolved in 1,4-dioxane (2 mL) and DMA (0.5 mL) then added 0.2 mL water, 6-chloro-3-(4,4,5,5-tetramethyl-1,3,2-dioxaborolan-2-yl)pyrazolo[1,5-a]pyrimidine (59.9 mg, 0.214 mmol) and KOAc (31.6 mg, 0.322 mmol). The mixture was degassed for 10 min then added tetrakistriphenylphosphine Pd(0) (25 mg, 0.021 mmol) and degassed for 5 minutes. The mixture was heated at 100° C. for 2 h in a microwave reactor. The reaction mixture was cooled, filtered, and the filtrate was concentrated under high vacuum. The residue was dissolved in DMF and purified via preparative HPLC to afford 2-(6-chloropyrazolo[1,5-a]pyrimidin-3-yl)-N-isopropyl-5-(4-propyl-1H-1,2,3-triazol-1-yl)pyridin-4-amine (9.7 mg, 18% yield). $^1$H NMR (500 MHz, DMSO-d$_6$) δ 9.75 (s, 1H), 8.99 (s, 1H), 8.93 (s, 1H), 8.43 (s, 1H), 8.33 (s, 1H), 7.90 (s, 1H), 7.27 (br. s., 1H), 3.97 (d, J=6.5 Hz, 0.5H), 3.58 (br. s., 0.5H), 2.73 (t, J=7.6 Hz, 2H), 1.72 (sxt, J=7.4 Hz, 2H), 1.27 (d, J=6.3 Hz, 6H), 0.99 (t, J=7.3 Hz, 3H).

TABLE 2

| Ex. No. | Structure | HPLC rt (min) | HPLC cond. | LCMS |
|---|---|---|---|---|
| 12 | 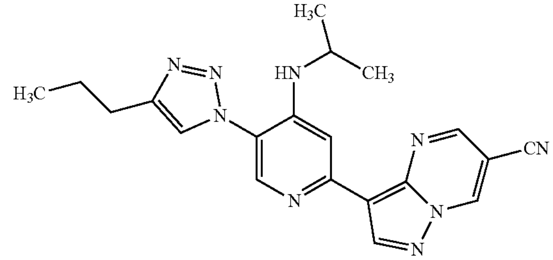 [SMILES: CCCc1cn(-c2cnc(-c3cnn4cc(C#N)cnc34)cc2NC(C)C)nn1] | 1.70 | C | 388.3 |

TABLE 2-continued

| Ex. No. | Structure | HPLC rt (min) | HPLC cond. | LCMS |
|---|---|---|---|---|
| 13 | ![structure 13] | 1.64 | C | 441.3 |
| 14 | ![structure 14] | 1.26 | C | 455.1 |

Example 15

3-(4-(isopropylamino)-5-(4-propyl-1H-1,2,3-triazol-1-yl)pyridin-2-yl)imidazo[1,2-b]pyridazine-7-carbonitrile (15)

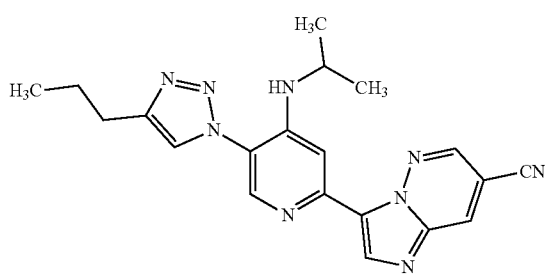

Intermediate 15A: N-isopropyl-5-(4-propyl-1H-1,2,3-triazol-1-yl)-2-(trimethylstannyl)pyridin-4-amine (15A)

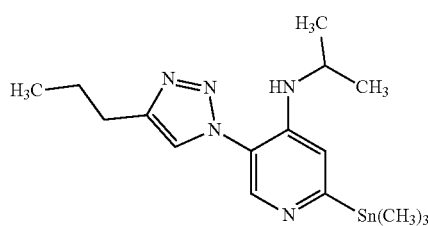

In a vial suitable for heating, a stirred solution of 2-chloro-N-isopropyl-5-(4-propyl-1H-1,2,3-triazol-1-yl)pyridin-4-amine (70 mg, 0.250 mmol), hexamethylditin (0.062 mL, 0.300 mmol) in toluene (4 mL) was degassed with nitrogen for 10 minutes. 1,1'-Bis(di-tert-butylphosphino)ferrocene palladium dichloride (11.73 mg, 0.018 mmol) was added and degassed for additional 5 minutes. The pressure tube was closed and heated to 110° C. for 3 h behind a safety shield. The mixture was allowed to come to room temperature and filtered. The solids were washed twice with toluene (2 mL), and the combined filtrate and rinsings were concentrated in vacuo to yield a brown oil (150 mg, 73% yield) which was used as-is immediately in the next step. LCMS 409.1 (M+H).

Example 15

In a 5 mL microwave tube, a mixture of N-isopropyl-5-(4-propyl-1H-1,2,3-triazol-1-yl)-2-(trimethylstannyl)pyridin-4-amine (100 mg, 0.184 mmol), 3-bromoimidazo[1,2-b]pyridazine-7-carbonitrile (41 mg, 0.184 mmol), and CuI (3.50 mg, 0.018 mmol) in dioxane (3 mL) was degassed nitrogen for 5 minutes. The mixture was treated with tetrakis(triphenylphosphine)Pd(0) (42.5 mg, 0.037 mmol), degassed for an additional 5 minutes, then the vial was sealed. The reaction mixture was heated via microwave reactor at 150° C. for 20 minutes. The reaction mixture was filtered, and the filtrate was concentrated under high vacuum. The residue was purified via preparative HPLC to afford 3-(4-(isopropyl amino)-5-(4-propyl-1H-1,2,3-triazol-1-yl)pyridin-2-yl) imidazo[1,2-b]pyridazine-7-carbonitrile (3.4 mg, 5% yield). $^1$H NMR (500 MHz, DMSO-$d_6$) δ 9.10 (d, J=7.2 Hz, 2H), 8.71 (br s, 1H), 8.52-8.32 (m, 2H), 8.12 (br s, 1H), 6.57 (d, J=7.2 Hz, 1H), 3.94-3.74 (m, 1H), 2.72 (t, J=7.3 Hz, 2H), 1.78-1.64 (m, 2H), 1.27 (d, J=6.2 Hz, 6H), 0.99 (t, J=7.2 Hz, 3H); LCMS 388.3 (M+H); HPLC rt 1.65 min, Conditions C.

Example 16

3-(4-(isopropylamino)-5-(1-(tetrahydro-2H-pyran-4-yl)-1H-1,2,3-triazol-4-yl)pyridin-2-yl)imidazo[1,2-b]pyridazine-7-carbonitrile

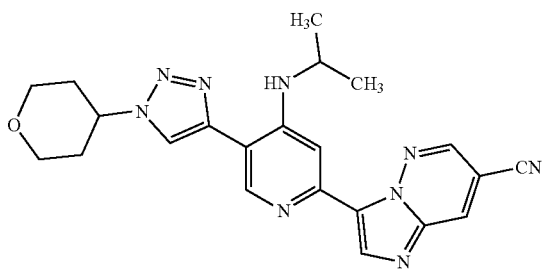

(16)

Intermediate 16A: Ethyl 6-chloro-4-(isopropylamino)nicotinate

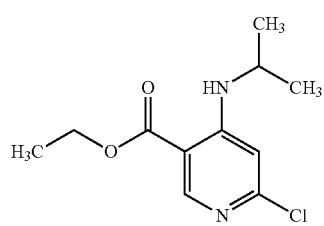

(16A)

In a heavy-walled flask equipped with a Teflon screw-cap, a mixture of ethyl 4,6-dichloronicotinate (12.3 g, 55.9 mmol), and isopropylamine (14.37 mL, 168 mmol) in ethanol (100 mL) stirred at 80° C. for 18 hours, at which point the reaction was judged to be complete by LCMS. The mixture was concentrated to dryness, and the crude material was chromatographed via MPLC over a 330 g silica gel column eluting with 0-10% ethyl acetate/hexanes. Fractions containing the product were pooled and concentrated in vacuo to yield ethyl 6-chloro-4-(isopropylamino)nicotinate (12.3 g, 90% yield) as a colorless solid. $^1$H NMR (400 MHz, chloroform-d) δ 8.69 (s, 1H), 8.11 (br. s., 1H), 6.56 (s, 1H), 4.36 (q, J=7.1 Hz, 2H), 3.71 (dq, J=13.3, 6.5 Hz, 1H), 1.41 (t, J=7.2 Hz, 3H), 1.31 (d, J=6.4 Hz, 6H); LCMS 243.1 (M+H)$^+$.

Intermediate 16B: (6-chloro-4-(isopropylamino)pyridin-3-yl)methanol

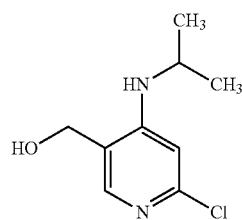

(16B)

A stirring solution of ethyl 6-chloro-4-(isopropylamino)nicotinate (1.42 g, 5.85 mmol) was cooled to −78° C., and treated drop wise with 1 M LAH in THF (18.14 mL, 18.14 mmol) over 10 minutes. When the addition was complete, the reaction mixture was stirred at −78° C. for 60 minutes, then allowed to warm to 0° C. The vessel was placed in an ice/water bath, and the reaction was carefully quenched with water (0.7 mL) followed by 1 M NaOH (2.8 mL). After stirring for 1 hour, the resulting insoluble powder was removed by filtration, rinsed thoroughly with THF, and the combined filtrate and rinsings were concentrated in vacuo to yield (6-chloro-4-(isopropylamino)pyridin-3-yl)methanol (1.14 g, 97% yield) as a colorless solid. LCMS 201.2 (M+H)+.

Intermediate 16C: 6-Chloro-4-(isopropylamino)nicotinaldehyde

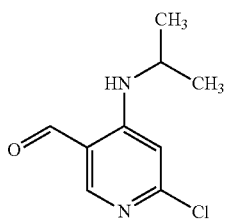

(16C)

A stirring solution of (6-chloro-4-(isopropylamino)pyridin-3-yl)methanol (1.14 g, 5.68 mmol) was treated with manganese dioxide (2.469 g, 28.4 mmol). The reaction mixture was stirred at room temperature for 60 hours (weekend), at which point it was judged to be complete by LCMS. The mixture was filtered, the solids were rinsed twice with THF and once with methylene chloride, and the combined filtrate and rinsings were concentrated in vacuo. The residue was chromatographed via MPLC over a 40 g silica gel column, eluting at 40 mL/min with 15-50% ethyl acetate/hexanes. Fractions containing the desired product were pooled and concentrated in vacuo to yield 6-chloro-4-(isopropylamino)nicotinaldehyde (967 mg, 86% yield) as a colorless oil. $^1$H NMR (400 MHz, chloroform-d) δ 9.84 (d, J=0.7 Hz, 1H), 8.56 (br. s., 1H), 8.30 (s, 1H), 6.60 (s, 1H), 3.81-3.66 (m, 1H), 1.33 (d, J=6.4 Hz, 6H); LCMS 199.2 (M+H)$^+$.

Intermediate 16D: 2-Chloro-5-ethynyl-N-isopropylpyridin-4-amine

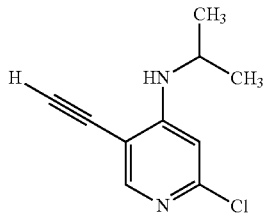

(16D)

A stirring mixture of 6-chloro-4-(isopropylamino)nicotinaldehyde (3.16 g, 15.91 mmol) and potassium carbonate (5.50 g, 39.8 mmol) in anhydrous methanol (30 mL) was cooled to 5° C. and treated with dimethyl (1-diazo-2-oxopropyl)phosphonate (7.64 mL, 31.8 mmol). The reaction mixture was allowed to warm to room temperature and stirred for 6 hours. LCMS showed that the reaction was incomplete. The mixture was treated with potassium carbonate (1.646 g, 11.93 mmol) and dimethyl (1-diazo-2-oxopropyl) phosphonate (1.5 g, 7.81 mmol). The reaction mixture was stirred at room temperature for 3 days, at which point it was judged to be complete by LCMS. Most of the methanol was evaporated with a stream of nitrogen, and the remaining mixture was poured into ethyl acetate (75 mL). The turbid solution was washed once with water, 2× with saturated sodium bicarbonate, and once with brine, then the organic phase was dried over sodium sulfate and concentrated in vacuo. The residue was chromatographed via MPLC over a 80 g silica gel column, eluting at 60 mL/min with a 15% to 50% ethyl acetate/hexanes gradient over 10 column volumes. Fractions containing the desired product were pooled and concentrated in vacuo to yield 2-chloro-5-ethynyl-N-isopropylpyridin-4-amine (2.26 g, 73% yield) as a purple solid. $^1$H NMR (400 MHz, chloroform-d) δ 8.13 (s, 1H), 6.48 (s, 1H), 4.97 (br. s., 1H), 3.70 (dq, J=13.5, 6.5 Hz, 1H), 3.53 (s, 1H), 1.30 (d, J=6.4 Hz, 6H); LCMS 194.9 (M+H)$^+$.

Intermediate 16E: 2-Chloro-N-isopropyl-5-(1-(tetrahydro-2H-pyran-4-yl)-1H-1,2,3-triazol-4-yl)pyridin-4-amine

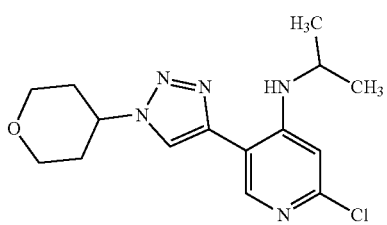

(16E)

In a sealed vial, a mixture of 4-azidotetrahydro-2H-pyran (111 mg, 0.873 mmol), 2-chloro-5-ethynyl-N-isopropylpyridin-4-amine (85 mg, 0.437 mmol), sodium ascorbate (17.30 mg, 0.087 mmol), and Cu(II) sulfate (6.97 mg, 0.044 mmol) was stirred at 50° C. for 2 hours, then at room temperature for 48 hours. The mixture was diluted with ethyl acetate (25 mL), and the turbid solution was washed 3× with water and once with brine, then dried over sodium sulfate and concentrated in vacuo. The residue was purified via column chromatography over a 24 g silica gel column, eluting at 40 mL/min with a 0.5% to 10% methanol/methylene chloride gradient over 10 column volumes. Fractions containing the desired product were pooled and concentrated in vacuo to yield 2-chloro-N-isopropyl-5-(1-(tetrahydro-2H-pyran-4-yl)-1H-1,2,3-triazol-4-yl)pyridin-4-amine (125 mg, 89% yield) as a colorless solid. LCMS 322.1 (M+H); $^1$H NMR (400 MHz, CHLOROFORM-d) δ 8.30-8.14 (m, 2H), 7.89 (s, 1H), 6.60 (s, 1H), 4.87-4.68 (m, 1H), 4.20 (dt, J=11.9, 3.4 Hz, 2H), 3.85-3.70 (m, 1H), 3.70-3.49 (m, 2H), 2.33-2.15 (m, 4H), 1.59 (s, 3H), 1.36 (d, J=6.4 Hz, 6H).

Intermediate 16F: N-isopropyl-5-(1-(tetrahydro-2H-pyran-4-yl)-1H-1,2,3-triazol-4-yl)-2-(trimethylstannyl)pyridin-4-amine

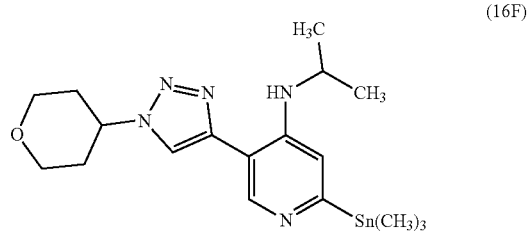

(16F)

In a 5 mL microwave vial, a mixture of 2-chloro-N-isopropyl-5-(1-(tetrahydro-2H-pyran-4-yl)-1H-1,2,3-triazol-4-yl)pyridin-4-amine (55 mg, 0.171 mmol) and hexamethylditin (0.043 mL, 0.205 mmol) in toluene (2 mL) was degassed with bubbling nitrogen for 5 minutes. The mixture was treated with 1,1'-bis(di-tert-butylphosphino) ferrocene palladium dichloride (11.1 mg, 0.017 mmol) and degassed for an additional 5 minutes, then the vial was sealed. The reaction mixture was heated at 80° C. for 18 hours. The mixture was allowed to come to room temperature and filtered. The solids were washed with toluene (1 mL), and the combined filtrate and rinsings were concentrated in vacuo to yield a dark brown oil which was used as-is in the next step.

Example 16

In a 5 mL microwave tube, a mixture of N-isopropyl-5-(1-(tetrahydro-2H-pyran-4-yl)-1H-1,2,3-triazol-4-yl)-2-(trimethylstannyl)pyridin-4-amine (77 mg, 0.17 mmol), 3-bromoimidazo[1,2-b]pyridazine-7-carbonitrile (45.5 mg, 0.204 mmol), and CuI (3.24 mg, 0.017 mmol) in dioxane (1 mL) was degassed with bubbling nitrogen for 5 minutes. The mixture was treated with tetrakis(triphenylphosphine)Pd(0) (39.3 mg, 0.034 mmol), degassed for an additional 5 minutes, then the vial was sealed. The reaction mixture was heated via microwave at 150° C. The solvents were evaporated, and the residue was taken up in DMSO (2 mL). The solution was filtered purified via preparative HPLC to afford 3-(4-(isopropylamino)-5-(1-(tetrahydro-2H-pyran-4-yl)-1H-1,2,3-triazol-4-yl)pyridin-2-yl)imidazo[1,2-b]pyridazine-7-carbonitrile (6 mg, 8% yield), $^1$H NMR (500 MHz, DMSO-d$_6$) δ 9.05 (br s, 1H), 9.01 (s, 1H), 8.88 (s, 1H), 8.69 (br s, 1H), 8.66 (s, 1H), 8.22 (d, J=6.9 Hz, 1H), 8.01 (s, 1H), 4.86 (br. s., 1H), 4.01 (d, J=12.8 Hz, 2H), 2.19-2.01 (m, 4H), 1.33 (d, J=6.2 Hz, 6H).

TABLE 3

| Ex. No. | Structure | HPLC rt (min) | HPLC cond. | LCMS |
|---|---|---|---|---|
| 17 | 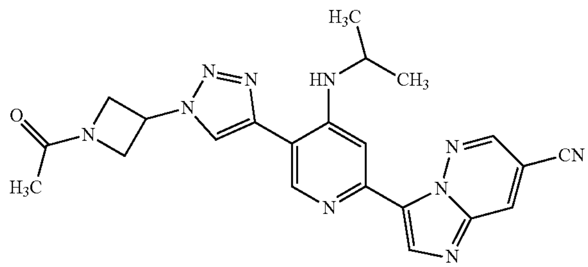 [SMILES: CC(=O)N1CC(n2cc(-c3cnc(-c4cnc5cc(C#N)cnn45)cc3NC(C)C)nn2)C1] | 1.21 | C | 443.3 |
| 18 | 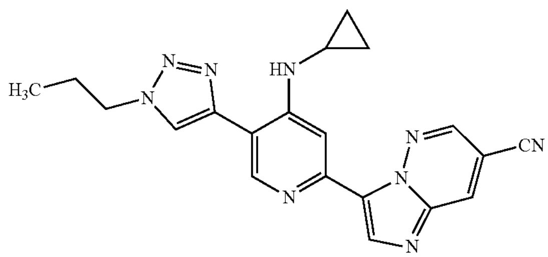 [SMILES: CCCn1cc(-c2cnc(-c3cnc4cc(C#N)cnn34)cc2NC2CC2)nn1] | 1.20 | F | 386.3 |
| 19 | 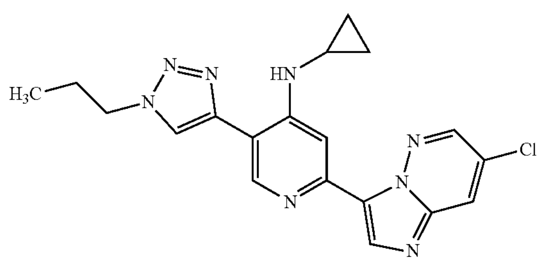 [SMILES: CCCn1cc(-c2cnc(-c3cnc4cc(Cl)cnn34)cc2NC2CC2)nn1] | 1.24 | F | 395.2 |
| 20 | 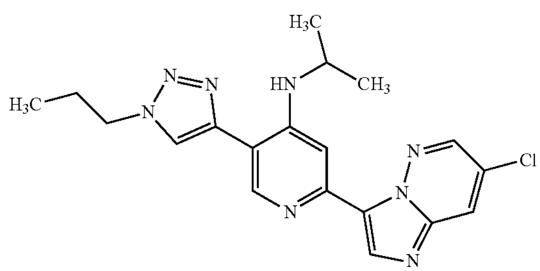 [SMILES: CCCn1cc(-c2cnc(-c3cnc4cc(Cl)cnn34)cc2NC(C)C)nn1] | 1.83 | C | 397.2 |
| 21 | 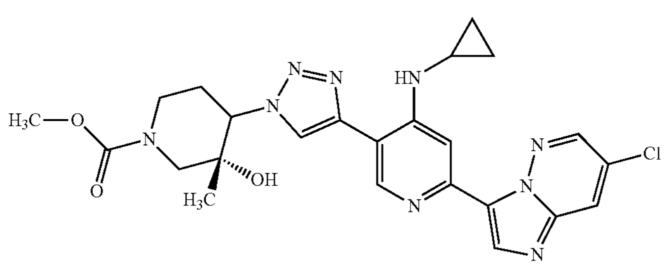 [SMILES: COC(=O)N1CCC(n2cc(-c3cnc(-c4cnc5cc(Cl)cnn45)cc3NC3CC3)nn2)[C@](C)(O)C1] | 1.65 | C | 524.2 |

TABLE 3-continued

| Ex. No. | Structure | HPLC rt (min) | HPLC cond. | LCMS |
|---|---|---|---|---|
| 22 | 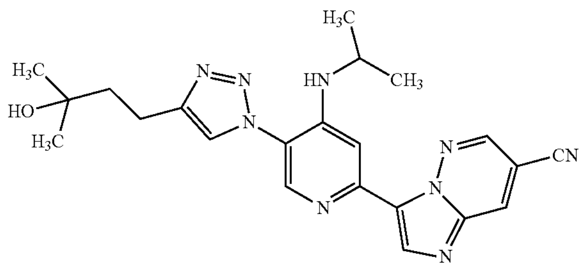 [SMILES: CC(C)Nc1cc(-c2cnc3cc(C#N)cnn23)ncc1-n1cc(CCC(C)(C)O)nn1] | 1.68 | E | 432.2 |
| 23 | 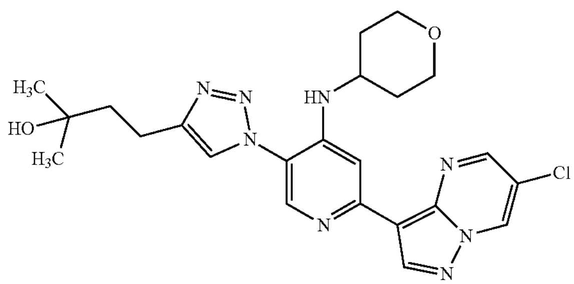 [SMILES: CC(C)(O)CCc1cn(-c2cnc(-c3cnn4cc(Cl)cnc34)cc2NC2CCOCC2)nn1] | 1.54 | E | 483.2 |
| 24 | 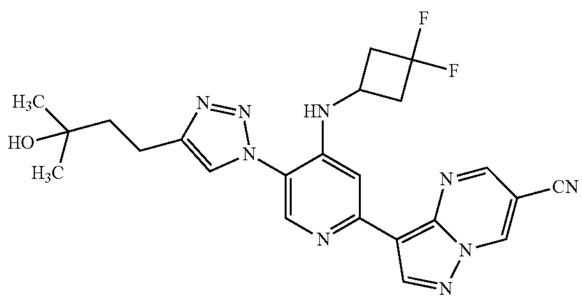 [SMILES: CC(C)(O)CCc1cn(-c2cnc(-c3cnn4cc(C#N)cnc34)cc2NC2CC(F)(F)C2)nn1] | 1.47 | E | 480.3 |
| 25 | 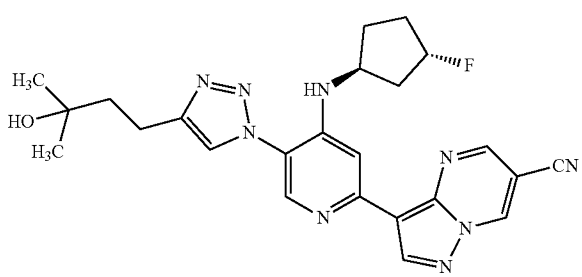 [SMILES: CC(C)(O)CCc1cn(-c2cnc(-c3cnn4cc(C#N)cnc34)cc2N[C@H]2CC[C@H](F)C2)nn1] | 1.69 | E | 476.1 |
| 26 | 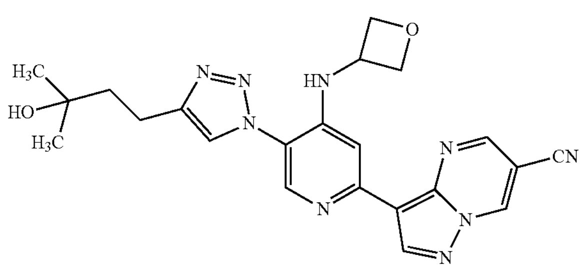 [SMILES: CC(C)(O)CCc1cn(-c2cnc(-c3cnn4cc(C#N)cnc34)cc2NC2COC2)nn1] | 1.32 | E | 466.1 |

Example 27

3-(5-(1-(3-hydroxy-3-methylbutyl)-1H-pyrazol-4-yl)-4-(isopropylamino)pyridin-2-yl) imidazo[1,2-b]pyridazine-7-carbonitrile (27)

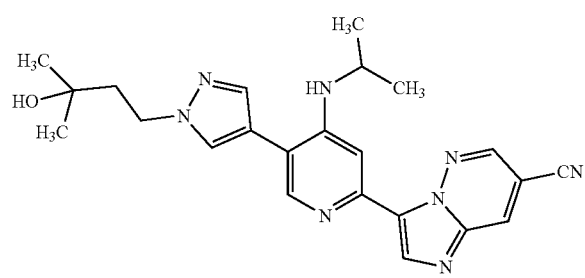

Intermediate 27A: Ethyl 6-chloro-4-(isopropylamino)nicotinate (27A)

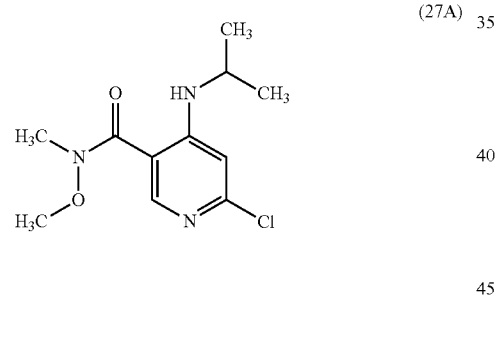

To a solution of 6-chloro-4-(isopropylamino)nicotinic acid (3 g, 14 mmol) in DMF (20 mL) were successively added HATU (5.31 g, 14 mmol), N,O-dimethylhydroxylamine hydrochloride (1.36 g, 14 mmol) and DIPEA (7.32 mL, 41.9 mmol). The reaction mixture was stirred for 18 h. The reaction mixture was concentrated in vacuo and then partitioned between water and ethylacetate. The layers were separated and the aqueous layer was further extracted with ethyl acetate. (3×). The combined organic layers were dried over $Na_2SO_4$, filtered, and concentrated in vacuo. The residue was purified via silica gel chromatography using 0-15% ethyl acetate/pet ether to afford compound 6-chloro-4-(isopropylamino)-N-methoxy-N-methylnicotinamide (3.2 g, 89% yield) as colorless syrup. $^1$H NMR (300 MHz, DMSO-$d_6$) δ 8.03 (s, 1H), 6.71 (s, 1H), 6.53 (d, J=7.8 Hz, 1H), 3.75 (m, 1H), 3.54 (s, 3H), 3.25 (s, 3H), 1.31 (m, 6H); LCMS 258.2 (M+H)$^+$.

Intermediate 27B: 1-(6-chloro-4-(isopropylamino)pyridin-3-yl)ethanone (27B)

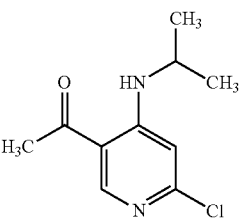

To a stirred solution of 6-chloro-4-(isopropylamino)-N-methoxy-N-methylnicotinamide (3.2 g, 12.42 mmol) in THF (45 mL) was added methylmagnesium bromide (12.42 mL, 37.3 mmol) at 0° C. The reaction mixture was allowed to warm to room temperature and stirring continued for 1 h. The reaction mixture was then cooled to −20° C. and quenched by the addition of $NH_4Cl$ (aq). The mixture was brought to room temperature and diluted with ethylacetate. The organic layer was separated and aqueous layer was extracted with ethylacetate (2×). The combined organic layers were dried over $Na_2SO_4$, filtered, and concentrated in vacuo to afford 1-(6-chloro-4-(isopropylamino)pyridin-3-yl)ethanone (2.5 g, 11.75 mmol, 95% yield) as pale yellow syrup, which was used without further purification. LCMS 213.1 (M+H)$^+$.

Intermediate 27C: 6-(6-chloro-4-(isopropylamino)pyridin-3-yl)-4,6-dioxohexanoic acid (27C)

To a solution of 1-(6-chloro-4-(isopropylamino)pyridin-3-yl)ethanone (1.0 g, 4.7 mmol) and dihydrofuran-2,5-dione (0.471 g, 4.7 mmol)[succinic anhydride] in THF was added potassium tert-butoxide (14.11 mL, 14.11 mmol, 1.0 M in THF) at room temperature. The resultant reddish solution was stirred overnight. An additional 7 mL of potassium tert-butoxide (1.0 M in THF) was added and stirring was continued for 8 h. The reaction mixture was diluted with water and extracted with ethylacetate. The aqueous layer was acidified with 1.5 N HCl and extracted with ethylacetate (3×). The combined organic layers were dried over $Na_2SO_4$, filtered, and concentrated in vacuo to afford 6-(6-chloro-4-(isopropylamino)pyridin-3-yl)-4,6-dioxohexanoic acid (800 mg, 54% yield), which was used without further purification.

Intermediate 27D: 3-(3-(6-chloro-4-(isopropylamino)pyridin-3-yl)-1H-pyrazol-5-yl) propanoic acid

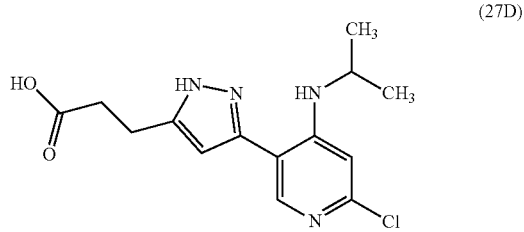 [SMILES: CC(C)Nc1cc(Cl)ncc1-c1cc(CCC(=O)O)[nH]n1]

(27D)

To a stirred solution of 6-(6-chloro-4-(isopropylamino)pyridin-3-yl)-4,6-dioxohexanoic acid (800 mg, 2.56 mmol) in ethanol (10 mL) was added hydrazine (0.080 mL, 2.56 mmol). The reaction mixture was stirred at room temperature for 3 h. The reaction mixture was concentrated in vacuo and suspended in water. The mixture was neutralized with 1.5 N HCl solution and the resulting solids were filtered and dried to afford 3-(3-(6-chloro-4-(isopropylamino)pyridin-3-yl)-1H-pyrazol-5-yl)propanoic acid (680 mg, 86% yield) as brown solid.

Intermediate 27E: ethyl 3-(3-(6-chloro-4-(isopropylamino)pyridin-3-yl)-1H-pyrazol-5-yl) propanoate

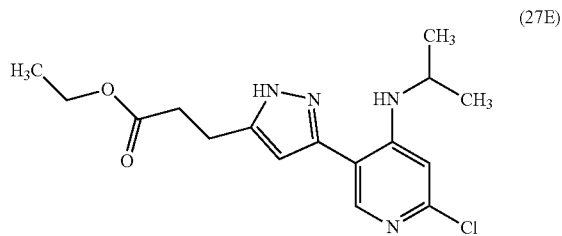 [SMILES: CCOC(=O)CCc1cc(-c2cnc(Cl)cc2NC(C)C)n[nH]1]

(27E)

To a stirred solution of 3-(3-(6-chloro-4-(isopropylamino)pyridin-3-yl)-1H-pyrazol-5-yl)propanoic acid (680 mg, 2.2 mmol) in ethanol (0.129 mL, 2.2 mmol) was added thionyl chloride (0.5 mL, 6.85 mmol) dropwise. The reaction mixture was heated at 65° C. for 3 h. The reaction mixture was concentrated and the resulting red syrup was treated with 10% NaHCO$_3$ solution. The resulting solids were filtered and dried in vacuo to give afford ethyl 3-(3-(6-chloro-4-(isopropylamino)pyridin-3-yl)-1H-pyrazol-5-yl) propanoate (550 mg, 1.633 mmol, 74.1% yield) as a pale red solid. $^1$H NMR (400 MHz, DMSO-d$_6$) δ 12.94 (s, 1H), 8.53-8.42 (m, 1H), 8.36-8.26 (m, 1H), 6.70-6.60 (m, 2H), 4.18-3.94 (m, 2H), 3.87-3.71 (m, 1H), 2.98-2.84 (m, 2H), 2.77-2.63 (m, 2H), 1.31-1.08 (m, 9H); LCMS m/z 337.4 (M+H)$^+$.

Intermediate 27F: 4-(3-(6-chloro-4-(isopropylamino)pyridin-3-yl)-1H-pyrazol-5-yl)-2-methylbutan-2-ol

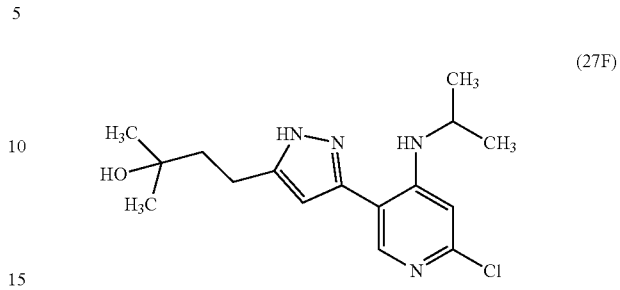

(27F)

To a stirred solution of ethyl 3-(3-(6-chloro-4-(isopropylamino)pyridin-3-yl)-1H-pyrazol-5-yl)propanoate (550 mg, 1.63 mmol) in THF (20 mL) was added methylmagnesium bromide (2.72 mL, 8.16 mmol) dropwise at 0° C. The reaction mixture was stirred for 2 h at 0° C. and then at room temperature for 18 h. The reaction mixture was cooled to −20° C. The reaction was quenched by the addition of aqueous NH$_4$Cl solution. The product was extracted with ethyl acetate (2×) and the combined organic layer was dried over Na$_2$SO$_4$, filtered, and concentrated. The product was purified via silica gel chromatography using 0-5% methanol/DCM to provide 4-(3-(6-chloro-4-(isopropylamino)pyridin-3-yl)-1H-pyrazol-5-yl)-2-methylbutan-2-ol (400 mg, 76% yield) as brown solid. $^1$H NMR (400 MHz, DMSO-d$_6$) δ 12.98-12.81 (m, 1H), 8.59-8.42 (m, 1H), 8.39-8.22 (m, 1H), 6.72-6.54 (m, 2H), 4.39-4.28 (br s, 1H), 3.86-3.72 (m, 1H), 2.76-2.62 (m, 2H), 1.78-1.64 (m, 2H), 1.34-0.94 (m, 12H); LCMS m/z 323.3 (M+H)$^+$.

Intermediate 27G: 4-(3-(4-(isopropylamino)-6-(trimethylstannyl)pyridin-3-yl)-1H-pyrazol-5-yl)-2-methylbutan-2-ol

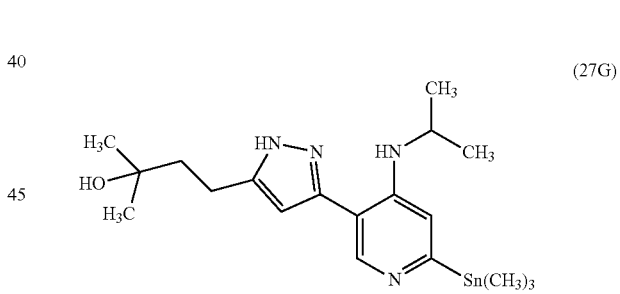

(27G)

A stirred solution of 4-(3-(6-chloro-4-(isopropylamino)pyridin-3-yl)-1H-pyrazol-5-yl)-2-methylbutan-2-ol (210 mg, 0.650 mmol) and hexamethylditin (0.162 mL, 0.781 mmol) in toluene (10 mL) was degassed for 10 minutes by bubbling Ar gas through the reaction mixture). 1,1'-Bis(di-tert-butylphosphine)ferrocene palladium dichloride (42.4 mg, 0.065 mmol) was added and degassed for additional 5 minutes. The pressure tube was closed and heated to 110° C. for 3 h. The reaction mixture was filtered and concentrated in vacuo to afford compound 4-(3-(4-(isopropylamino)-6-(trimethylstannyl)pyridin-3-yl)-1H-pyrazol-5-yl)-2-methylbutan-2-ol (250 mg, 85% yield) as black syrup which was used further without purification.

Example 27

To a stirred solution of 4-(3-(4-(isopropylamino)-6-(trimethylstannyl)pyridin-3-yl)-1H-pyrazol-5-yl)-2-methylbutan-2-ol (121 mg, 0.269 mmol) in dioxane (4 mL)[in a pressure tube] was added 3-bromoimidazo[1,2-b]pyridazine-7-carbonitrile (50 mg, 0.224 mmol) and the mixture was degassed with Argon for 10 minutes. To this mixture, Pd(Ph$_3$P)$_4$ (52 mg, 0.045 mmol) was added and degassed for additional 5 minutes. The pressure tube was closed and heated at 110° C. for 16 h. The reaction mixture was filtered through an analytical filter, thoroughly washed with ethyl acetate and concentrated to give the crude compound. The product was purified via preparative HPLC to afford 3-(5-(5-(3-hydroxy-3-methylbutyl)-1H-pyrazol-3-yl)-4-(isopropylamino)pyridin-2-yl)imidazo[1,2-b]pyridazine-7-carbonitrile (13.2 mg, 13.5% yield). $^1$H NMR (400 MHz, DMSO-d$_6$) δ 13.21 (s, 1H), 9.21-9.19 (m, 2H), 8.85 (s, 1H), 8.74 (s, 1H), 7.90 (s, 1H), 6.88 (s, 1H), 4.50 (br s, 1H), 4.12-4.07 (m, 1H), 2.76-2.72 (m, 2H), 1.77-1.73 (m, 2H), 1.38 (d, J=6.4 Hz, 6H), 1.15 (s, 6H).

only reactions for 0% inhibition. The final concentrations of reagents in the assays are ATP, 500 μM; FL-IPTSPITT-TYFFFKKK peptide 1.5 μM; IRAK4, 0.6 nM; and DMSO, 1.6%.

Caco-2 Permeability Assay Protocol

Thirteen to 27 days prior to assay, Caco-2 cells were seeded onto collagen-coated polycarbonate filter membranes in 24-well transwell plates at a density of 1.45×10$^5$ cells/cm$^2$, approximately 4.8×10$^4$ cells per well. The cells were grown in a culture medium consisting of DMEM supplemented with 10% fetal bovine serum, 10 mM HEPES, 1% nonessential amino acids, 2 mM L-glutamine, 100 U/mL penicillin-G, and 100 μg/mL streptomycin. The culture medium was replaced every 3 days and the cells were maintained at 37° C. in a 95% relative humidity and 5% CO$_2$ atmosphere. The cells were evaluated for tight junction formation just prior to assay. The test compound was solubilized to 10 mM in 100% DMSO and diluted to 3 μM in assay buffer. Permeability studies were initiated by adding 200 μL assay buffer plus/minus compound to the apical transwell compartment and 600 μL assay buffer plus/minus compound to the basolateral compartment of the 24-well transwell low-binding cluster plate. For apical-to-basolateral (A to B) permeability (absorptive direction), buffer containing compound was placed in the apical compartment (donorwells), while buffer alone was placed in the corresponding basolateral compartments (receiverwells). For basolateral-to-apical (B to A) permeability (secretive direction), buffer containing compound was placed in the basolateral compartment (donor wells), while buffer alone was placed in the corresponding apical compartments (receiver wells). Transwells were then incubated for 2 hours at 37° C. in a 95% relative humidity and 5% CO$_2$ atmosphere with gentle agitation. Following incubation, 100 μL was removed from each apical and basolateral compartment and transferred to 96-well low binding plates that had been previously loaded with 100 μL/well of acetonitrile containing 250 nM propranolol, 250 nM diclofenac, and 500 nM tolbutamide as

TABLE 4

| Ex. No. | Structure | HPLC rt (min) | HPLC cond. | LCMS |
|---|---|---|---|---|
| 28 | 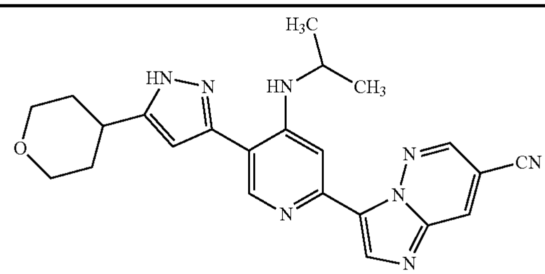 | 1.68 | E | 429.2 |
| 29 | 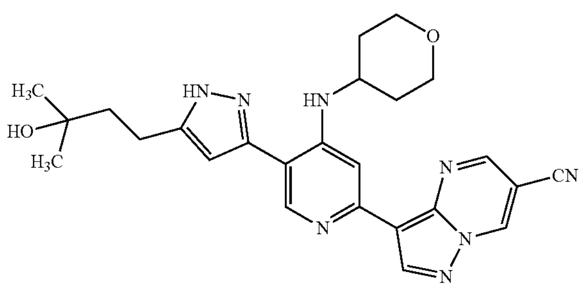 [SMILES: CC(C)(O)CCc1cc(-c2cnc(-c3cnn4cc(C#N)cnc34)cc2NC2CCOCC2)n[nH]1] | 1.53 | E | 473.2 |

Biological Assays

The pharmacological properties of the compounds of this invention may be confirmed by a number of biological assays. The exemplified biological assays, which follow, have been carried out with compounds of the invention.

IRAK4 Inhibition Assay

The assays were performed in U-bottom 384-well plates. The final assay volume was 30 μL prepared from 15 μL additions of enzyme and substrates (fluoresceinated peptide and ATP) and test compounds in assay buffer (20 mM HEPES pH 7.2, 10 mM MgCl$_2$, 0.015% Brij 35 and 4 mM DTT). The reaction was initiated by the combination of IRAK4 with substrates and test compounds. The reaction mixture was incubated at room temperature for 60 min. and terminated by adding 45 μL of 35 mM EDTA to each sample. The reaction mixture was analyzed on the Caliper LAB-CHIP® 3000 (Caliper, Hopkinton, Mass.) by electrophoretic separation of the fluorescent substrate and phosphorylated product. Inhibition data were calculated by comparison to no enzyme control reactions for 100% inhibition and vehicleinternal standards. The samples were subsequently analyzed by LC-MS/MS to determine concentrations of compound.

IRAK4 Whole Blood Assay

Human whole blood containing the anti-coagulant ACD-A was plated in 384-well plate (25 μL/well) and incubated with compounds for 60 minutes at 37° C. in a 5% $CO_2$ incubator. The blood was stimulated with a TLR2 agonist, 10 μg/mL final concentration of lipoteichoic acid (Invivogen, San Diego, Calif.) in 25 μL RPMI (Gibco) for 5 hours in a 5% $CO_2$ incubator. At the end of the incubation, plates were centrifuged at 2300 rpm for 5 minutes. Supernatants were harvested and analyzed for IL-6 levels by Flow Cytometry beads assay (BD Biosciences, San Jose, Calif.).

PBMC TLR2 Induced IL-6 Assay.

Peripheral blood mononuclear cells (PBMCs) were isolated from human blood containing the anti-coagulant EDTA (2.5 mM) by centrifugation over a Ficoll gradient. PBMCs (250000 cells/well) were cultured in assay media (RPMI with 10% heat inactivated FCS) with compounds for 30 minutes at 37° C. in a 5% $CO_2$ incubator. Following pretreatment with compounds, cells were stimulated for 5 hours with 10 μg/ml lipoteichoic acid (Invivogen, San Diego, Calif.), a TLR2 agonist. At the end of the culture, plates were centrifuged at 1800 rpm for 10 minutes to pellet the cells. Supernatants were harvested and analyzed for L-6 levels by ELISA (BD Biosciences, San Jose, Calif.).

The table below lists the IRAK4 $IC_{50}$ values, the Whole Blood $EC_{50}$ values, and Caco-2 Permeability values for the following examples of this invention measured in the IRAK4 Inhibition Assay, IRAK4 Whole Blood Assay and the Caco-2 Permeability assay. The compounds of the present invention, as exemplified by the following examples, showed IRAK $IC_{50}$ inhibition values of less than 0.6 μM.

TABLE 4

| Example No. | IRAK4 $IC_{50}$ (μM) | Whole Blood $EC_{50}$ (μM) | Caco-2 Permeability (nm/s) |
|---|---|---|---|
| 1 | 0.578 | — | — |
| 2 | 0.063 | — | — |
| 3 | 0.014 | 1.03 | — |
| 4 | 0.396 | — | — |
| 5 | 0.174 | — | — |
| 6 | 0.018 | 4.41 | — |
| 7 | 0.053 | — | — |
| 8 | 0.043 | — | — |
| 9 | 0.029 | — | — |
| 10 | 0.020 | — | — |
| 11 | 0.008 | — | 179 |
| 12 | 0.009 | — | 347 |
| 13 | 0.003 | 0.95 | — |
| 14 | 0.009 | 0.82 | — |
| 15 | 0.006 | 1.78 | 225 |
| 16 | 0.002 | — | — |
| 17 | 0.002 | — | — |
| 18 | 0.002 | 0.18 | 225 |
| 19 | 0.003 | 2.32 | — |
| 20 | 0.012 | — | — |
| 21 | 0.014 | 2.87 | — |
| 22 | 0.004 | 0.78 | 295 |
| 23 | 0.009 | 0.99 | — |
| 24 | 0.014 | 0.78 | — |
| 25 | 0.005 | 0.25 | 134 |
| 26 | 0.010 | 0.16 | — |
| 27 | 0.003 | 0.62 | 136 |
| 28 | 0.005 | 0.59 | — |
| 29 | 0.002 | 0.51 | — |

What is claimed is:

1. A compound of Formula (I)

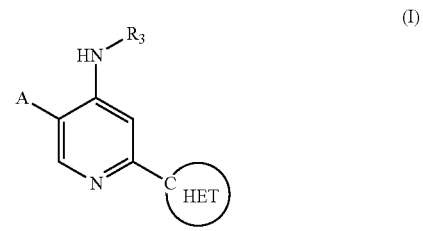

or a salt thereof, wherein:

HET is a heteroaryl selected from imidazo[1,2-b] pyridazinyl and pyrazolo[1,5-a] pyrimidinyl, wherein said heteroaryl is attached to the pyridinyl group in the compound of Formula (I) by a carbon ring atom in said heteroaryl and wherein said heteroaryl is substituted with zero to 2 $R_b$;

A is pyrazolyl, imidazolyl, or triazolyl, each substituted with zero or 1 $R_a$;

$R_3$ is:
(i) —$CH_2CH_3$, —$CH(CH_3)_2$, —$CH_2CHF_2$, —CH($CH_3$)$CH_2OH$, oxetanyl, tetrahydropyranyl, or $C_{3-5}$ cycloalkyl substituted with zero to 2 F; or
(ii) pyrazolyl substituted with zero to 2 substituents independently selected from $C_{1-3}$ alkyl, $C_{1-3}$ hydroxyalkyl, $C_{1-3}$ fluoroalkyl, oxetanyl, tetrahydrofuranyl, and tetrahydropyranyl;

$R_a$ is:
(i) F, Cl, —OH, —CN, $C_{1-6}$ alkyl, $C_{1-4}$ fluoroalkyl, $C_{1-4}$ cyanoalkyl, or $C_{1-6}$ hydroxyalkyl; or
(ii) $C_{3-6}$ cycloalkyl, azetidinyl, oxetanyl, tetrahydrofuranyl, tetrahydropyranyl, piperidinyl, piperazinyl, pyrrolyl, pyrrolidinonyl, morpholinyl, pyrrolidinyl, phenyl, pyrazolyl, imidazolyl, pyridinyl, or pyrimidinyl, each substituted with zero to 4 substituents independently selected F, —CN, —OH, —$NR_yR_y$, $C_{1-3}$ alkyl, $C_{1-3}$ fluoroalkyl, —CH(phenyl)$_2$, —O($C_{1-4}$ alkyl), —C(O)($C_{1-4}$ alkyl), —C(O)($C_{1-4}$ deuteroalkyl), —C(O)($C_{3-6}$ cycloalkyl), —C(O)O ($C_{1-4}$ alkyl), —C(O)$NR_yR_y$, —C(O)(phenyl), —C(O)(pyridinyl), —C(O)$CH_2$($C_{3-6}$ cycloalkyl), —NHC(O)$CH_3$, —NHC(O)$OCH_3$, —NHC(O)OC($CH_3$)$_3$, —S(O)$_2$($C_{1-3}$ alkyl), and —OS(O)$_2$($C_{1-3}$ alkyl);

each $R_b$ is independently selected from F, Cl, —CN, —$NH_2$, —$CH_3$, —$OCH_3$, and cyclopropyl;

and each $R_y$ is independently H or $C_{1-3}$ alkyl.

2. The compound according to claim 1 or a salt thereof, wherein:

HET is a heteroaryl selected from imidazo[1,2-b] pyridazinyl and pyrazolo[1,5-a] pyrimidinyl, wherein said heteroaryl is attached to the pyridinyl group in the compound of Formula (I) by a carbon ring atom in said heteroaryl and wherein said heteroaryl is substituted with zero to 2 $R_b$;

A is pyrazolyl, imidazolyl, or triazolyl, each substituted with zero or 1 $R_a$;

$R_3$ is:
(i) —$CH_2CH_3$, —$CH(CH_3)_2$, —$CH_2CHF_2$, —CH($CH_3$)$CH_2OH$, cyclopropyl, oxetanyl, or tetrahydropyranyl; or
(ii) pyrazolyl substituted with zero to 2 substituents independently selected from $C_{1-3}$ alkyl, $C_{1-3}$ hydroxyalkyl, $C_{1-3}$ fluoroalkyl, oxetanyl, tetrahydrofuranyl, and tetrahydropyranyl;

$R_a$ is:
(i) F, Cl, —OH, —CN, $C_{1-6}$ alkyl, $C_{1-4}$ fluoroalkyl, $C_{1-4}$ cyanoalkyl, or $C_{1-6}$ hydroxyalkyl; or
(ii) $C_{3-6}$ cycloalkyl, azetidinyl, oxetanyl, tetrahydrofuranyl, tetrahydropyranyl, piperidinyl, piperazinyl, pyrrolyl, pyrrolidinonyl, morpholinyl, pyrrolidinyl, phenyl, pyrazolyl, imidazolyl, pyridinyl, or pyrimidinyl, each substituted with zero to 4 substituents independently selected F, —CN, —OH, —$NR_yR_y$, $C_{1-3}$ alkyl, $C_{1-3}$ fluoroalkyl, —CH(phenyl)$_2$, —O($C_{1-4}$ alkyl), —C(O)($C_{1-4}$ alkyl), —C(O)($C_{1-4}$ deuteroalkyl), —C(O)($C_{3-6}$ cycloalkyl), —C(O)O ($C_{1-4}$ alkyl), —C(O)$NR_yR_y$, —C(O)(phenyl), —C(O)(pyridinyl), —C(O)CH$_2$($C_{3-6}$ cycloalkyl), —NHC(O)CH$_3$, —NHC(O)OCH$_3$, —NHC(O)OC (CH$_3$)$_3$, —S(O)$_2$($C_{1-3}$ alkyl), and —OS(O)$_2$($C_{1-3}$ alkyl);

each $R_b$ is independently selected from F, Cl, —CN, —NH$_2$, —CH$_3$, —OCH$_3$, and cyclopropyl;

and each $R_y$ is independently H or $C_{1-3}$ alkyl.

3. The compound according to claim 1 or a salt thereof, wherein:
HET is a heteroaryl selected from imidazo[1,2-b]pyridazinyl and pyrazolo[1,5-a] pyrimidinyl, wherein said heteroaryl is attached to the pyridinyl group in the compound of Formula (I) by a carbon ring atom in said heteroaryl and wherein said heteroaryl is substituted with zero to 1 $R_b$;
A is pyrazolyl or triazolyl, each substituted with zero or 1 $R_a$;
$R_3$ is —CH(CH$_3$)$_2$, cyclopropyl, difluorocyclobutyl, fluorocyclopentyl, oxetanyl, tetrahydropyranyl, or 2,2-difluoroethyl pyrazolyl;
$R_a$ is —OH, —CH$_3$, —CH$_2$CH$_2$CH$_3$, —CH$_2$CF$_3$, —C(CH$_3$)$_2$OH, —CH$_2$C(CH$_3$)$_2$OH, —CH$_2$CH$_2$C (CH$_3$)$_2$OH, tetrahydropyranyl, acetylazetidinyl, or

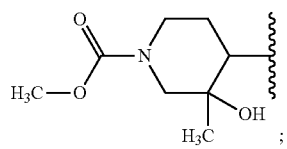

;

and $R_b$ is Cl or —CN.

4. The compound according to claim 1 or a salt thereof, wherein:
HET is a heteroaryl selected from imidazo[1,2-b]pyridazinyl and pyrazolo[1,5-a] pyrimidinyl, wherein said heteroaryl is attached to the pyridinyl group in the compound of Formula (I) by a carbon ring atom in said heteroaryl and wherein said heteroaryl is substituted with zero to 1 $R_b$;
A is pyrazolyl or triazolyl, each substituted with zero or 1 $R_a$;
$R_3$ is —CH(CH$_3$)$_2$, cyclopropyl, or 2,2-difluoroethyl pyrazolyl;
$R_a$ is —OH, —CH$_3$, —CH$_2$CH$_2$CH$_3$, —CH$_2$CF$_3$, —C(CH$_3$)$_2$OH, —CH$_2$C(CH$_3$)$_2$OH, —CH$_2$CH$_2$C (CH$_3$)$_2$OH, tetrahydropyranyl, acetylazetidinyl, or

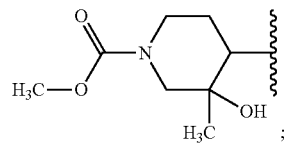

;

and $R_b$ is Cl or —CN.

5. The compound according to claim 1 or a salt thereof, wherein:
A is

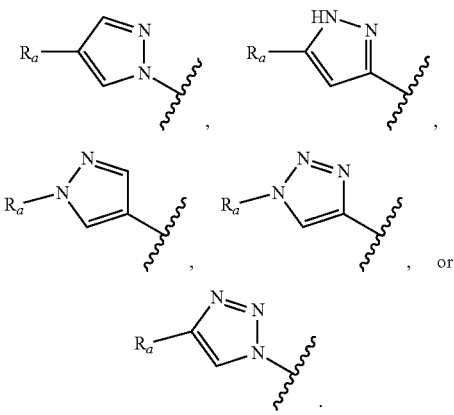

6. The compound according to claim 1 or a salt thereof, wherein:
A is

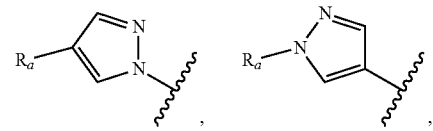

7. The compound according to claim 1 or a salt thereof, wherein HET is:

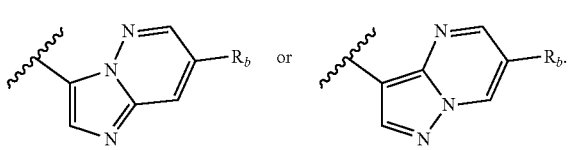

8. The compound according to claim 1 or a salt thereof, wherein:
HET is

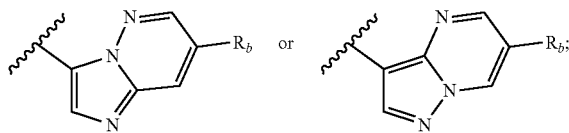

R₃ is —CH(CH₃)₂, cyclopropyl,

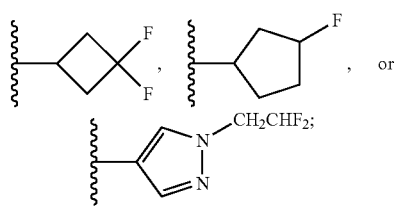

and
R_b is Cl or —CN.

9. The compound according to claim 1 or a salt thereof, wherein A is pyrazolyl.

10. The compound according to claim 1 or a salt thereof, wherein A is triazolyl.

11. The compound according to claim 1 or a salt thereof, wherein said compound is selected from: 3-(5-(4-(2-hydroxypropan-2-yl)-1H-pyrazol-1-yl)-4-(isopropylamino)pyridin-2-yl) pyrazolo[1,5-a]pyrimidine-6-carbonitrile (1); 2-(7-chloroimidazo[1,2-b] pyridazin-3-yl)-N-isopropyl-5-(4-(tetrahydro-2H-pyran-4-yl)-1H-pyrazol-1-yl)pyridin-4-amine (2); 3-(4-(isopropylamino)-5-(1-(tetrahydro-2H-pyran-4-yl)-1H-pyrazol-4-yl) pyridin-2-yl)imidazo[1,2-b]pyridazine-7-carbonitrile (3); 1-(4-(6-(7-chloroimidazo[1,2-b] pyridazin-3-yl)-4-(isopropylamino)pyridin-3-yl)-1H-pyrazol-1-yl)-2-methylpropan-2-ol (4); 3-(5-(1-(2-hydroxy-2-methylpropyl)-1H-pyrazol-4-yl)-4-(isopropylamino)pyridin-2-yl)imidazo[1,2-b]pyridazine-7-carbonitrile (5); 3-(4-(isopropylamino)-5-(1-propyl-1H-pyrazol-4-yl)pyridin-2-yl)imidazo[1,2-b]pyridazine-7-carbonitrile (6); 2-(7-chloroimidazo[1,2-b]pyridazin-3-yl)-N-isopropyl-5-(1-(2,2,2-trifluoroethyl)-1H-pyrazol-4-yl)pyridin-4-amine (7); 3-(4-(isopropylamino)-5-(1-(2,2,2-trifluoroethyl)-1H-pyrazol-4-yl)pyridin-2-yl)imidazo[1,2-b]pyridazine-7-carbonitrile (8); 2-(7-chloroimidazo[1,2-b] pyridazin-3-yl)-N-(1-(2,2-difluoroethyl)-1H-pyrazol-4-yl)-5-(1-propyl-1H-pyrazol-4-yl)pyridin-4-amine (9); 3-(4-((1-(2,2-difluoroethyl)-1H-pyrazol-4-yl)amino)-5-(1-propyl-1H-pyrazol-4-yl)pyridin-2-yl) imidazo[1,2-b]pyridazine-7-carbonitrile (10); 2-(6-chloropyrazolo[1,5-a]pyrimidin-3-yl)-N-isopropyl-5-(4-propyl-1H-1,2,3-triazol-1-yl) pyridin-4-amine (11); 3-(4-(isopropylamino)-5-(4-propyl-1H-1,2,3-triazol-1-yl)pyridin-2-yl)pyrazolo[1,5-a]pyrimidine-6-carbonitrile (12); 4-(1-(6-(6-chloropyrazolo[1,5-a] pyrimidin-3-yl)-4-(isopropylamino)pyridin-3-yl)-1H-1,2,3-triazol-4-yl)-2-methylbutan-2-ol (13); 4-(1-(6-(6-chloropyrazolo[1,5-a]pyrimidin-3-yl)-4-(oxetan-3-ylamino)pyridin-3-yl)-1H-1,2,3-triazol-4-yl)-2-methylbutan-2-ol (14); 3-(4-(isopropylamino)-5-(4-propyl-1H-1,2,3-triazol-1-yl)pyridin-2-yl) imidazo[1,2-b]pyridazine-7-carbonitrile (15); 3-(4-(isopropylamino)-5-(1-(tetrahydro-2H-pyran-4-yl)-1H-1,2,3-triazol-4-yl)pyridin-2-yl) imidazo[1,2-b]pyridazine-7-carbonitrile (16); 3-(5-(1-(1-acetylazetidin-3-yl)-1H-1,2,3-triazol-4-yl)-4-(isopropylamino)pyridin-2-yl)imidazo [1,2-b]pyridazine-7-carbonitrile (17); 3-(4-(cyclopropylamino)-5-(1-propyl-1H-1,2,3-triazol-4-yl)pyridin-2-yl)imidazo [1,2-b]pyridazine-7-carbonitrile (18); 2-(7-chloroimidazo[1,2-b]pyridazin-3-yl)-N-cyclopropyl-5-(1-propyl-1H-1,2,3-triazol-4-yl)pyridin-4-amine (19); 2-(7-chloroimidazo [1,2-b]pyridazin-3-yl)-N-isopropyl-5-(1-propyl-1H-1,2,3-triazol-4-yl)pyridin-4-amine (20); (3R)-methyl 4-(4-(6-(7-chloroimidazo[1,2-b] pyridazin-3-yl)-4-(cyclopropylamino) pyridin-3-yl)-1H-1,2,3-triazol-1-yl)-3-hydroxy-3-methylpiperidine-1-carboxylate (21); 3-(5-(4-(3-hydroxy-3-methylbutyl)-1H-1,2,3-triazol-1-yl)-4-(isopropylamino)pyridin-2-yl) imidazo[1,2-b]pyridazine-7-carbonitrile (22); 4-(1-(6-(6-chloropyrazolo[1,5-a] pyrimidin-3-yl)-4-((tetrahydro-2H-pyran-4-yl)amino)pyridin-3-yl)-1H-1,2,3-triazol-4-yl)-2-methylbutan-2-ol (23); 3-(4-((3,3-difluorocyclobutyl)amino)-5-(4-(3-hydroxy-3-methylbutyl)-1H-1,2,3-triazol-1-yl)pyridin-2-yl)pyrazolo[1,5-a]pyrimidine-6-carbonitrile (24); 3-(4-(((1S,3S)-3-fluorocyclopentyl)amino)-5-(4-(3-hydroxy-3-methylbutyl)-1H-1,2,3-triazol-1-yl)pyridin-2-yl)pyrazolo[1,5-a]pyrimidine-6-carbonitrile (25); 3-(5-(4-(3-hydroxy-3-methylbutyl)-1H-1,2,3-triazol-1-yl)-4-(oxetan-3-ylamino)pyridin-2-yl) pyrazolo[1,5-a]pyrimidine-6-carbonitrile (26); 3-(5-(1-(3-hydroxy-3-methylbutyl)-1H-pyrazol-4-yl)-4-(isopropylamino)pyridin-2-yl) imidazo[1,2-b]pyridazine-7-carbonitrile (27); 3-(4-(isopropylamino)-5-(5-(tetrahydro-2H-pyran-4-yl)-1H-pyrazol-3-yl)pyridin-2-yl)imidazo[1,2-b]pyridazine-7-carbonitrile (28); and 3-(5-(5-(3-hydroxy-3-methylbutyl)-1H-pyrazol-3-yl)-4-((tetrahydro-2H-pyran-4-yl)amino)pyridin-2-yl)pyrazolo[1,5-a] pyrimidine-6-carbonitrile (29).

12. A pharmaceutical composition comprising one or more compounds according to claim 1 and a pharmaceutically acceptable carrier or diluent.

* * * * *

UNITED STATES PATENT AND TRADEMARK OFFICE
CERTIFICATE OF CORRECTION

PATENT NO. : 10,202,390 B2
APPLICATION NO. : 15/738435
DATED : February 12, 2019
INVENTOR(S) : John V. Duncia et al.

It is certified that error appears in the above-identified patent and that said Letters Patent is hereby corrected as shown below:

In the Claims

Claim 1, Column 58, Line 40, delete "F," and insert -- from F, --, therefor.

Claim 2, Column 59, Line 12 (Approx.), delete "F," and insert -- from F, --, therefor.

Claim 11, Column 62, Lines 34-35, delete "(((1S,3 S)-" and insert -- (((1S,3S)- --, therefor.

Signed and Sealed this
Third Day of September, 2019

Andrei Iancu
*Director of the United States Patent and Trademark Office*